(12) United States Patent
Edens et al.

(10) Patent No.: US 7,879,804 B2
(45) Date of Patent: Feb. 1, 2011

(54) BLOOD PRESSURE LOWERING PEPTIDES IN A SINGLE ENZYMATIC STEP

(75) Inventors: Luppo Edens, Rotterdam (NL); Andre de Roos, Delft (NL); Olaf Leonardus Schouten, Delft (NL); Philippus Antonius Deen, Leiden (NL)

(73) Assignee: DSM IP Assets B.V., Te Heerlen (NL)

( * ) Notice: Subject to any disclaimer, the term of this patent is extended or adjusted under 35 U.S.C. 154(b) by 453 days.

(21) Appl. No.: 11/793,390

(22) PCT Filed: Dec. 21, 2005

(86) PCT No.: PCT/EP2005/057000

§ 371 (c)(1),
(2), (4) Date: Jun. 19, 2007

(87) PCT Pub. No.: WO2006/067163

PCT Pub. Date: Jun. 29, 2006

(65) Prior Publication Data

US 2008/0113896 A1    May 15, 2008

(30) Foreign Application Priority Data

Dec. 22, 2004  (EP) .................................. 04106859

(51) Int. Cl.
*A61K 38/06* (2006.01)
(52) U.S. Cl. .............................. 514/18; 435/68.1; 514/2
(58) Field of Classification Search ...................... 514/2, 514/18; 435/68.1
See application file for complete search history.

(56) References Cited

U.S. PATENT DOCUMENTS

| | | | |
|---|---|---|---|
| 6,180,761 B1 * | 1/2001 | Han et al. .................... | 530/360 |
| 6,994,987 B1 * | 2/2006 | Yamamoto et al. ......... | 435/68.1 |
| 7,309,595 B2 * | 12/2007 | Dekker et al. ............... | 435/212 |
| 2005/0148504 A1 * | 7/2005 | Katunuma et al. ............ | 514/12 |
| 2007/0054352 A1 * | 3/2007 | van der Burg-Koorevaar et al. ......................... | 435/68.1 |

FOREIGN PATENT DOCUMENTS

| | | |
|---|---|---|
| EP | 0 583 074 A2 | 2/1994 |
| EP | 1 231 279 A1 | 8/2002 |
| WO | WO 01/68115 A1 | 9/2001 |
| WO | WO 01/81366 A2 | 11/2001 |
| WO | WO 01/81368 A2 | 11/2001 |
| WO | 2004/098309 A1 | 11/2004 |
| WO | WO 2006/005757 A2 | 1/2006 |
| WO | WO 2006/089921 A1 | 8/2006 |

OTHER PUBLICATIONS

Greenberg (J Biol Chem 259, 5132-5138, 1984).*
Yoshimoto, J. Biol. Chem. 255, 4786-4792, 1980.*
Heins, Biochimica et Biophysica Acta 954, 161-169, 1988.*
Jimenez-Flores, Biochemical and Biophysical Research Communications 142(2), 617-621, 1987.*
Sipola et al, "Effect of Long-Term Intake of Milk Products on Blood Pressurein Hypertensive Rats", Journal Dairy Research, Cambridge, GB, vol. 69, 2002, pp. 103-111.

* cited by examiner

*Primary Examiner*—David Lukton
(74) *Attorney, Agent, or Firm*—Nixon & Vanderhye P.C.

(57) ABSTRACT

A process to produce IPP and VPP from a protein source that comprises the -I-P-P- and -V-P-P- sequence in its protein sequence and whereby at least 40% of -I-P-P- sequence present in the protein source is converted into the peptide IPP and at least 40% of the -V-P-P- sequence present in the protein source is converted into the peptide VPP, which comprises the use of a proline specific endoprotease and an amino-peptidase preferably in a single enzymatic step.

19 Claims, 4 Drawing Sheets

BLOOD PRESSURE LOWERING PEPTIDES IN A SINGLE ENZYMATIC STEP

This application is the US national phase of international application PCT/EP2005/057000 filed 21 Dec. 2005 which designated the U.S. and claims benefit of EP 04106859.4, dated 22 Dec. 2004, the entire content of which is hereby incorporated by reference.

FIELD OF THE INVENTION

The present invention relates to the production of IPP, LPP and VPP.

BACKGROUND OF THE INVENTION

Hypertension is a relatively common disease state in humans and presents a prevalent risk factor for cardiovascular diseases, kidney failure and stroke. The availability of a large array of pharmaceutical products such as calcium blockers, beta blockers, diuretics, alpha blockers, central alpha antagonists, angiotensin II antagonists and ACE inhibitors, illustrates that the underlying physiological mechanisms for hypertension are manysided.

Of the physiological mechanisms for hypertension, especially the renin-angiotensin mechanism has received a lot of scientific attention. In this mechanism, angiotensin is secreted by the liver and is cleaved by the peptidase renin to yield the biologically inactive decapeptide angiotensin I. As angiotensin I passes through the lung capillaries, another peptidase called angiotensin converting enzyme (hereinafter referred to as ACE) acts on angiotensin I by removing the last two residues of angiotensin I (His-Leu) to form the octapeptide angiotensin II. The angiotensin II octapeptide exhibits strong vasoconstricting activity and therefore raises blood pressure. ACE inhibition leading to lower levels of the angiotensin II prevents vasoconstriction and thus high blood pressures.

Apart from cleaving angiotensin I, ACE can also hydrolyse bradykinin, a nonapeptide also participating in blood pressure regulation. In the latter mechanism ACE inhibition leads to increased bradykinin levels which promote vasodilatation and lower blood pressure as well. Inhibiting ACE thus leads to blood pressure lowering effects via at least two separate mechanisms.

It is also known that the octapeptide angiotensin II stimulates the release of aldosterone by the adrenal cortex. The target organ for aldosterone is the kidney where aldosterone promotes increased reabsorbtion of sodium from the kidney tubules. Also via this third mechanism ACE inhibition reduces blood pressure but in this case by diminishing sodium reabsorption.

Because of its multiple physiological effects, inhibiting the proteolytic activity of ACE is an effective way of depressing blood pressure. This observation has resulted in a number of effective pharmaceutical blood pressure lowering products such as captopril and enalapril (Ondetti, M. A. et al., 1977, Science, Washington D.C., 196, 441-444).

Because hypertension is a relatively common disease state it would be advantageous to counteract this undesirable result of modern life style with mildly active natural ingredients. Especially mildly active natural ingredients that can be incorporated into food or beverage products because such products are consumed on a regular basis. Alternatively such mildly active natural ingredients could be incorporated into dietary supplements. During the last decades it has been discovered that specific peptides present in fermented milk have an ACE inhibiting capacity and can induce blood pressure reductions in hypertensive subjects. Nowadays numerous in vitro and a few animal trials have demonstrated ACE inhibiting effects of different peptides obtained from a variety of protein sources. Although in vitro ACE inhibition assays have revealed many different peptide sequences, it has to be emphasized that ACE inhibiting peptides need to circulate in the blood to exert an in vivo effect. The implication is that efficacious ACE inhibiting peptides should resist degradation by the gastrointestinal proteolytic digestion system and should remain intact during a subsequent transport over the intestinal wall.

A structure-function study of the various ACE inhibiting peptides has suggested that they often posses a Pro-Pro, Ala-Pro or Ala-Hyp at their C-terminal sequence (Maruyama, S. and Suzuki, H., 1982; Agric Biol. Chem., 46 (5): 1393-1394). This finding is partly explained by the fact that ACE is a peptidyl dipeptidase (EC3.4.15.1) unable to cleave peptide bonds involving proline. Thus from tripeptides having the structure Xaa-Pro-Pro the dipeptide Pro-Pro cannot be removed because the Xaa-Pro bond cannot be cleaved. It is therefore conceivable that if present in relatively high concentrations, tripeptides having the Xaa-Pro-Pro structure will inhibit ACE activity. As not only ACE but almost all proteolytic enzymes have difficulties in cleaving Xaa-Pro or Pro-Pro bonds, the notion that the presence of (multiple) proline residues at the carboxyterminal end of peptides results in relatively protease resistant molecules is almost self-evident. Similarly peptides containing hydroxyproline (Hyp) instead of proline are relatively protease resistant. From this it can be inferred that peptides carrying one or more (hydroxy)proline residues at their carboxyterminal end are likely to escape from proteolytic degradation in the gastrointestinal tract. These conclusions will help us to understand the remarkable in vivo blood pressure lowering effect of specific ACE inhibiting peptides: not only do they meet the structural requirements for ACE inhibition, they also resist degradation by the gastrointestinal proteolytic digestion system and remain intact during a subsequent transport over the intestinal wall.

Strong ACE inhibiting activities have been reported for the tripeptides Leu-Pro-Pro (JP02036127), Val-Pro-Pro (EP 0 583 074) and Ile-Pro-Pro (J. Dairy Sci., 78:777-7831995)). Initially all ACE inhibiting peptides were characterized on the basis of their in vitro effect on ACE activity and the tripeptides Ile-Pro-Pro (hereinafter referred to as IPP) Val-Pro-Pro (hereinafter referred to as VPP) and Leu-Pro-Pro (hereinafter referred to as LPP) stood out because of their strong ACE inhibiting effect resulting in relatively low IC50 values. Later on the presumed antihypertensive effects of the tripeptides VPP as well as IPP could be confirmed in spontaneously hypertensive rats (Nakamura et al., J. Dairy Sci., 78:12531257 (1995)). In these experiments the inhibitory tripeptides were derived from lactic acid bacteria fermented milk. During the milk fermentation the desirable peptides are produced by proteinases produced by the growing lactic acid bacteria. A drawback of this fermentative approach is that lactic acid bacteria are living organisms for which the type and quantity of excreted enzymes are difficult to control. The production of the ACE inhibiting peptides is therefore hardly reproducible and it is also unlikely that the optimal set of enzymes is being produced to ensure the maximal yield of the required peptides. Also the required fermentation times are relatively long which in combination with the low yields implies an unfavorable cost structure for the bioactive peptides. Moreover a fermented product is less suitable for direct incorporation into a.o. solid foods and creates strict organoleptic limitations. The poor palatability of such fermented milk products and the many processing difficulties encountered during the recovery of ACE inhibiting peptides from such fermented broths have been described in U.S. Pat. No. 6,428,812. Despite these disadvantages fermented milk products have been put to practical application as an orally administered vasodepressor. ACE inhibiting peptides have been concentrated from fermented milk products after electrodialysis, hollow fiber membrane dialysis or chromatographic methods to enable their marketing in the form of concentrated dietary supplements like tablets or lozenges.

The above mentioned drawbacks of the fermentative production route were recognized in a.o. patent applications WO 01/68115 and EP 1 231 279. In the latter application a purely enzymatic process is described to recover the tripeptides Val-Pro-Pro and Ile-Pro-Pro from milk casein. The application claims a method for producing these tripeptides by digesting material containing a milk casein with a proteinase and a peptidase via an intermediate peptide. Each of these enzyme incubations may take as long as 12 hours and take place under conditions that favor outgrowth of microbial contaminants. Prior to incubation with the peptidase, the intermediate peptide is preferably purified and high end concentrations of ACE inhibiting peptides can only be obtained after an additional chromatographic purification step of the intermediate peptide. In view of these various disadvantages, there is an obvious need for a more simple and microbiologically more reliable enzyme route that generates a bland tasting product with a high and reproducible yield of antihypertensive peptides.

SUMMARY OF THE INVENTION

The present invention relates to a process in which the peptides IPP and VPP are generated in high yields. The process comprises preferably a single enzyme incubation step. The present process comprises the use of a proteolytic enzyme or protease, which cleaves at the carboxy terminus of proline, preferably a proline specific endoprotease or a proline specific oligopeptidase, more preferably a proline specific endoprotease, in combination with a suitable aminopeptidase. Preferably the protease which cleaves at the terminus of proline, such as the proline specific endoprotease, as well as the aminopeptidase activity are free from any contaminating endoprotease activities. Preferably the protease which cleaves at the terminus of proline such as the proline specific endoprotease, as well as the aminopeptidase activity are free from contaminating carboxypeptidase activities. Proline specific endo protease which is free from contaminating endoprotease activity is an enzyme preparation having preferably an Prol Spec act/Endo ratio of more than 1, more preferable more than 100. Aminopeptidase activity which is free from contaminating endoprotease activity is an enzyme preparation having preferably an AP/Endo ratio of at least 0.1, more preferable at least 0.5 and most preferable at least 1.

Prolines specific endoprotease which is free for contaminating carboxyl peptidase activity is an enzyme preparation having preferably an Pro Spec act/CPD ratio of at least 1, more preferable of at least 10.

Amino peptidase activity which is free from contaminating carboxyl peptidase activity is an enzyme preparation having preferable an AP/CPD of at least 0.1, more preferable of at least 0.3. The above mentioned ratios are determined as described in Example 9.

Preferably at least 40%, more preferably at least 50%, or still more preferably at least 60% and most preferably at least 70% of -I-P-P- sequences present in the protein sequence is converted into the peptide IPP. Preferably at least 40%, more preferably at least 50%, or still more preferably at least 60% and most preferably at least 70% of -V-P-P-sequences present in the protein sequence is converted into the peptide VPP. Preferably at least 40%, more preferably at least 50%, or still more preferably at least 60% and most preferably at least 70% of -L-P-P- sequences present in the protein sequence is converted into the peptide LPP. The proline specific endoprotease is preferably capable of hydrolyzing large protein molecules like polypeptides or the protein itself. The process according to the invention has in general an incubation time of less than 24 hours, preferably the incubation time is less than 10 hours and more preferably less than 4 hours. The incubation temperature is in general higher than 30° C., preferably higher than 40° C. and more preferably higher than 50° C. During the production of IPP and VPP advantageously LPP is also formed. Another aspect of the present invention is a process to purify ACE inhibitory peptides from the other hydrolysed protein, preferably hydrolysed by a non-aspartic protease, more preferably by a serine protease. Part of the hydrolysed protein will precipitate under selected pH conditions. The purification process comprises altering the pH to the pH whereby the hydrolysed protein partly precipitates thus separating the precipitated proteins from the ACE inhibitory peptides in solution. In a further embodiment efficient and convenient recovery of the ACE inhibitory peptides the hydrolysed protein is mixed with a water soluble solvent to precipitate the bulk of the proteins.

The present invention further relates to the use of these peptide compositions, for the manufacture of a nutraceutical, preferably a medicament, for the improvement of health or the prevention and/or treatment of diseases or for the manufacture of a nutraceutical preferably a medicament, for the treatment or prevention of high blood pressure (hypertension), heart failure, pre-diabetes or diabetes, obesity, impaired glucose tolerance or stress.

Preferably the present peptide compositions are used in the form of a dietary supplement, in the form of a personal care application including a topical application in the form of a lotion, gel or an emulsion or as a food, beverage, feed or pet food ingredient.

The present invention further discloses
  a peptide composition suitable for the treatment of hypertensive blood pressure obtained by acid or solvent precipitation process having a proline content of 15 to 30% (w/w), preferably higher than 18% (w/w), more preferably higher than 20% (w/w) on dry matter,
  a peptide composition comprising
  5-20 mg/g VPP (on dry matter and on protein), 5-20 mg/g IPP (on dry matter and on protein) and optionally 5-20 mg/g LPP (on dry matter and on protein), and
  a peptide composition comprising 15-50% (wt dry matter) peptides containing at least a carboxy terminal proline and which comprises least 5 mg/g VPP (on dry matter and on protein), at least 5 mg/g IPP (on dry matter and on protein) and optionally at least 5 mg/g LPP (on dry matter and on protein).

DETAILED DESCRIPTION OF THE INVENTION

Effective ACE inhibiting peptides are likely to incorporate one or two proline residues at the carboxyterminal end of the peptide. The same structural requirement also endows peptides with increased resistance against proteolytic degradation hereby increasing the probability that the intact peptide will end up in the blood stream. To obtain peptides with at least a single but preferably multiple proline residues at their carboxyterminal end, the use of a protease that can cleave at the carboxyterminal side of proline residues offers an interesting option. So called prolyl oligopeptidases (EC 3.4.21.26) have the unique possibility of preferentially cleaving peptides at the carboxyl side of proline residues. In all adequately characterized proline specific proteases isolated from mammalian as well as microbial sources, a unique peptidase domain has been identified that excludes large peptides from the enzyme's active site. In fact these enzymes are unable to degrade peptides containing more than about 30 amino acid residues so that these enzymes are now referred to as "prolyl oligopeptidases" (Fulop et al: Cell, Vol. 94, 161-170, Jul. 24, 1998). As a consequence these prolyl oligopeptidases require an extensive pre-hydrolysis with other endoproteases before they can exert their hydrolytic action. However, as described in WO 02/45523, even the combination of a prolyl oligopeptidase with such another endoprotease results in hydrolysates characterized by a significantly enhanced proportion of peptides with a carboxyterminal proline residue. Because of this, such hydrolysates form an excellent starting point for the isolation of peptides with in vitro ACE inhibiting effects as well as an improved resistance to gastro-intestinal proteolytic degradation. Despite these potential benefits, we are not aware of an application specifying the use of proline specific proteases for the recovery of ACE inhibiting peptides let alone the selective production of IPP and VPP.

Furthermore the present invention relates to a process to produce a composition comprising soluble peptides which is produced by hydrolysing a protein with a proline specific endoproteases to a DH of 5-38%.

According to the present invention the process to obtain high amounts of IPP and VPP can be obtained preferably at a degree of hydrolysis (DH) of between 10 and 38, more preferably at a DH of between 15 and 35 and most preferably at a DH of between 20 and 30. The protein used in the present process is preferably a milk protein, more preferably casein or a caseinate. Advantageously the milk protein is not fermented before it is used in the present process. Preferably the insoluble part of the hydrolysed protein is separated from the soluble part under selected pH conditions, preferably acid pH conditions, more preferably at pH between 3.5 and 6 and most preferably at pH between 4 and 5 to result in the composition comprising soluble peptides. In another embodiment of the present invention the amino peptidase is only added after the separation of the insoluble part of the hydrolysed protein.

A "peptide" or "oligopeptide" is defined herein as a chain of at least two amino acids that are linked through peptide bonds. The terms "peptide" and "oligopeptide" are considered synonymous (as is commonly recognized) and each term can be used interchangeably as the context requires. A "polypeptide" is defined herein as a chain comprising of more than 30 amino acid residues. All (oligo)peptide and polypeptide formulas or sequences herein are written from left to right in the direction from amino-terminus to carboxy-terminus, in accordance with common practice. The one-letter code of amino acids used herein is commonly known in the art and can be found in Sambrook, et al. (Molecular Cloning: A Laboratory Manual, 2nd, ed. Cold Spring Harbor Laboratory, Cold Spring Harbor Laboratory Press, Cold Spring Harbor, N.Y., 1989).

The internationally recognized schemes for the classification and nomenclature of all enzymes from IUMB include proteases. The updated IUMB text for protease EC numbers can be found at the internet site: http://www.chem.qmw/ac.uk/iubmb/enzyme/EC3/4/11/. In this system enzymes are defined by the fact that they catalyze a single reaction. This has the important implication that several different proteins are all described as the same enzyme, and a protein that catalyses more than one reaction is treated as more than one enzyme. The system categorises the proteases into endo- and exoproteases. Endoproteases are those enzymes that hydrolyze internal peptide bonds, exoproteases hydrolyze peptide bonds adjacent to a terminal a-amino group ("aminopeptidases"), or a peptide bond between the terminal carboxyl group and the penultimate amino acid ("carboxypeptidases"). The endoproteases are divided into sub-subclasses on the basis of catalytic mechanism. There are sub-subclasses of serine endoproteases (EC 3.4.21), cysteine endoproteases (EC 3.4.22), aspartic endoproteases (EC 3.4.23), metalloendoproteases (EC 3.4.24) and threonine endoproteases (EC 3.4.25).

The aminopeptidases are in class 3.4.11. Sub-classification is on the basis of the relative efficiency with which the 20 different amino acids are removed. Aminopeptidases with a narrow and a broad specificity can be distinguished. Aminopeptidases can sequentially remove a single amino-terminal amino acids from protein and peptide substrates. Aminopeptidases with a narrow specificity exhibit a strong preference for the type of amino acid residue at the P1 position that is liberated from the substrate peptide. Aminopeptidases of broad specificity are capable of releasing a range of different amino acids at the N-terminal or P1 positions (according to Schechter's nomenclature: Schechter, I. And Berger, A. 1967. Biochem Biophys Res Commun 27:157-162). Carboxypeptidases can sequentially remove single carboxy-terminal amino acids from protein and peptide substrates. Comparable with the situation for the endoproteases, carboxypeptidases are divided into sub-subclasses on the basis of catalytic mechanism The serine-type carboxypeptidases are in class EC 3.4.16, the metallocarboxypeptidases in class EC 3.4.17 and the cysteine-type carboxypeptidases in class EC 3.4.18. The value of the EC list for proteases resides in providing standard terminology for the various types of protease activity and especially in the assignment of a unique identification number and a recommended name to each protease. The special strength of the EC system is thus in the area of nomenclature rather than classification.

In EP 1 231 279 a purely enzymatic process is described to recover the tripeptides Val-Pro-Pro and Ile-Pro-Pro from milk casein. The application claims a method for producing tripeptides by digesting a material containing a milk casein with a proteinase and a peptidase via a so called "intermediate peptide" selected from the group consisting of a peptide containing a sequence Val-Pro-Pro but containing no Pro other than those in this sequence as well as a peptide containing a sequence Ile-Pro-Pro but containing no Pro other than those in this sequence. As described in the Examples of EP 1 231 279 the method involves a two-step process. First the intermediate peptides encompassing either Val-Pro-Pro or Ile-Pro-Pro are produced. This is done by incubating casein with a suitable proteinase. According to one of the Examples at 37 degrees C. for a 12 hours period. Then the proteinase used is inactivated by heating this first hydrolysate to 100 degrees C. for 3 minutes and, after cooling down again, another enzyme preparation (in fact a preparation with exoproteolytic activity) is added. After another 12 hours incubation at 37 degrees C. with this other enzyme preparation the presence of the tripeptides Val-Pro-Pro and Ile-Pro-Pro can be demonstrated. To obtain higher yields of these ACE inhibiting peptides, EP 1 231 279 further suggests to purify and concentrate the intermediate peptide prior to exposure to the exoproteolytic activity. EP 1 231 279 also suggests that after obtaining the intermediate peptide and before the intermediate peptide is contacted with the peptidase in the procedure various operations may optionally be performed such as the removal of the unreacted protein by e.g. centrifugation at 5000 to 20000 rpm for 3 to 10 minutes. So the desired tripeptides are obtained in an industrially rather unwieldy two-step enzymatic process. As each of the enzyme incubations may take as long as 12 hours at pH 4.5 to 7.0 and at the temperature of 25 to 50 degrees C., it is evident that this procedure is also unacceptable from a microbiological point of view. These long incubation times combined with low incubation temperature of 25 to 50° C. may easily result in infections of the protein containing solution.

Thus according to the present invention IPP and VPP are enzymatically produced without purification of an intermediate product. EP 1231279 describes the formation of an intermediate peptide when milk protein is digested with a proteinase, which intermediate peptide contains no Pro other then the Ile-Pro-Pro or Val-Pro-Pro sequence, respectively. Subsequently, this intermediate peptide is converted with another enzyme to IPP or VPP, respectively. In order to obtain high yields, this intermediate peptide is chromatographically purified before converting to the tripeptide. According to the present invention high yields can be obtained without purifying an intermediate peptide.

Preferably at least 10 molar, more preferably at least 20 molar % and even more preferably at least 30 molar % of the soluble peptides of the process of the present invention have a carboxy terminal proline. In patent application WO 02/45523 it is described how this molar % can be determined.

The present invention relates to a peptide containing composition for use as a nutraceutical, preferably a medicament. The invention also relates to the use of present peptide containing composition as a nutraceutical preferably a medicament, to the use of present peptide containing composition for the manufacture of a nutraceutical preferably a medicament, to the use of the present peptide containing composition for the improvement of health or the prevention and/or treatment of diseases, to the use of the present peptide containing composition for the manufacture of a nutraceutical preferably a medicament, to the use of the present peptide containing composition for the treatment of cardiovascular diseases such as hypertension and heart failure, to the use of the present peptide containing composition for the treatment of pre-diabetes or diabetes, to the use of the present peptide containing composition for the treatment or prevention of obesity, to the use of the present peptide containing composition to increase plasma insulin or to increase the sensitivity for plasma insulin, to the use of the present peptide containing composition to increase plasma insulin or to increase the sensitivity for plasma insulin of type 2 diabetes or pre-diabetes, to the use of the present peptide containing composition to lower post-prandial glucose concentrations in blood of type 2 diabetes or pre-diabetes, to the use of the present peptide containing composition to increase post-prandial insulin secretion in blood of type 2 diabetes or pre-diabetes, to the use of the present peptide containing composition wherein the present peptide containing composition is in the form of a dietary supplement, to the use of the present peptide containing composition for the manufacture of a functional food product for the therapeutic treatment of the effects of stress, to the use of the present peptide containing composition in topical application preferably in personal care application and to the use of the present peptide containing composition in feed and pet food.

Furthermore the present invention relates to a method of treatment of type 1 and 2 diabetes, and for the prevention of type 2 diabetes in those individuals with pre-diabetes, or impaired glucose tolerance (IGT) which comprises administering to a subject in need of such treatment the present peptide containing composition and to a method of treatment of people that suffer of hypertension or heart failure or the prevention thereof which comprises administering to a subject in need of such treatment the present peptide containing composition and thus, exhibit blood pressure lowering effects. Inhibition of ACE results in reduced vasoconstriction, enhanced vasodilation, improved sodium and water excretion, which in turn leads to reduced peripheral vascular resistance and blood pressure and improved local blood flow. Thus, the present hydrolysates, comprising peptide, are particularly efficacious for the prevention and treatment of diseases that can be influenced by ACE inhibition, which include but are not limited to hypertension, heart failure, angina pectoris, myocardial infarction, stroke, peripheral arterial obstructive disease, atherosclerosis, nephropathy, renal insufficiency, erectile dysfunction, endothelial dysfunction, left ventricular hypertrophy, diabetic vasculopathy, fluid retention, and hyperaldosteronism. The compositions may also be useful in the prevention and treatment of gastrointestinal disorders (diarrhea, irritable bowel syndrome), inflammation, diabetes mellitus, obesity, dementia, epilepsy, geriatric confusion, and Meniere's disease. Furthermore, the compositions may enhance cognitive function and memory (including Alzheimer's disease), satiety feeling, limit ischemic damage, and prevent reocclusion of an artery after by-pass surgery or angioplasty.

Diabetes mellitus is a widespread chronic disease that hitherto has no cure. The incidence and prevalence of diabetes mellitus is increasing exponentially and it is among the most common metabolic disorders in developed and developing countries. Diabetes mellitus is a complex disease derived from multiple causative factors and characterized by impaired carbohydrate, protein and fat metabolism associated with a deficiency in insulin secretion and/or insulin resistance. This results in elevated fasting and postprandial serum glucose concentrations that lead to complications if left untreated. There are two major categories of the disease, insulin-dependent diabetes mellitus (IDDM, T1DM) and non-insulin-dependent diabetes mellitus (NIDDM, T2DM). T1DM=type 1 diabetes mellitus. T2DM=type 2 diabetes mellitus.

T1DM and T2DM diabetes are associated with hyperglycemia, hypercholesterolemia and hyperlipidemia. The absolute insulin deficiency and insensitivity to insulin in T1DM and T2DM, respectively, leads to a decrease in glucose utilization by the liver, muscle and the adipose tissue and to an increase in the blood glucose levels. Uncontrolled hyperglycemia is associated with increased and premature mortality due to an increased risk for microvascular and macrovascular diseases, including nephropathy, neuropathy, retinopathy, hypertension, stroke, and heart disease. Recent evidence showed that tight glycemic control is a major factor in the prevention of these complications in both T1DM and T2DM. Therefore, optimal glycemic control by drugs or therapeutic regimens is an important approach for the treatment of diabetes.

Therapy of T2DM initially involves dietary and lifestyle changes, when these measures fail to maintain adequate glycemic control the patients are treated with oral hypoglycemic agents and/or exogenous insulin. The current oral pharmacological agents for the treatment of T2DM include those that potentate insulin secretion (sulphonylurea agents), those that improve the action of insulin in the liver (biguanide agents), insulin-sensitizing agents (thiazolidinediones) and agents which act to inhibit the uptake of glucose (α-glucosidase inhibitors). However, currently available agents generally fail to maintain adequate glycemic control in the long term due to progressive deterioration of hyperglycemia, resulting from progressive loss of pancreatic cell function. The proportion of patients able to maintain target glycemia levels decreases markedly over time necessitating the administration of additional/alternative pharmacological agents. Furthermore, the drugs may have unwanted side effects and are associated with high primary and secondary failure rates. Finally, the use of hypoglycemic drugs may be effective in controlling blood glucose levels, but may not prevent all the complications of diabetes. Thus, current methods of treatment for all types of diabetes mellitus fail to achieve the ideals of normoglycemia and the prevention of diabetic complications.

Therefore, although the therapies of choice in the treatment of T1DM and T2DM are based essentially on the administration of insulin and of oral hypoglycemic drugs, there is a need for a safe and effective nutritional supplement with minimal side effects for the treatment and prevention of diabetes. Many patients are interested in alternative therapies which could minimize the side effects associated with high-dose of drugs and yield additive clinical benefits. Patients with diabetes mellitus have a special interest in treatment considered as "natural" with mild anti-diabetic effects and without major side effects, which can be used as adjuvant treatment. T2DM is a progressive and chronic disease, which usually is not recognized until significant damage has occurred to the pancreatic cells responsible for producing insulin (β-cells of islets of Langerhans). Therefore, there is an increasing interest in the development of a dietary supplement that may be used to prevent β-cell damage and thus, the progression to overt T2DM in people at risk especially in elderly who are at high risk for developing T2DM. Protection of pancreatic β-cells may be achieved by decreasing blood glucose and/or lipid levels as glucose and lipids exert damaging effects on β-cells. The reduction of blood glucose levels can be achieved via different mechanisms, for example by enhancing insulin sensitivity and/or by reducing hepatic glucose production. The reduction of blood lipid levels can also be achieved via different mechanisms, for example by enhancing lipid oxidation and/or lipid storage. Another possible strategy to protect pancreatic β-cells would be to decrease oxidative stress. Oxidative stress also causes β-cell damage with subsequent loss of insulin secretion and progression to overt T2DM.

Therefore, T2DM is a complicated disease resulting from coexisting defects at multiple organ sites: resistance to insulin action in muscle and adipose tissues, defective pancreatic insulin secretion, unrestrained hepatic glucose production. Those defects are often associated with lipid abnormalities and endothelial dysfunction. Given the multiple pathophysiological lesions in T2DM, combination therapy is an attractive approach to its management.

The present invention relates to novel nutraceutical compositions comprising the peptide containing composition of the present invention. The nutraceutical compositions comprising the peptide containing composition of the present invention can also comprise unhydrolysed proteins and carbohydrates as the active ingredients for the treatment or prevention of diabetes mellitus, or other conditions associated with impaired glucose tolerance such as syndrome X. In another aspect the present invention relates to the use of such compositions as a nutritional supplement for the said treatment or prevention, e.g., as an additive to a multi-vitamin preparations comprising vitamins and minerals which are essential for the maintenance of normal metabolic function but are not synthesized in the body. In still another aspect, the invention relates to a method for the treatment of both type 1 and 2 diabetes mellitus and for the prevention of T2DM in those individuals with pre-diabetes, or impaired glucose tolerance (IGT) or obesity which comprises administering to a subject in need of such treatment the peptide containing composition of the present invention and protein hydrolysates or unhydrolysed proteins and/or carbohydrates.

The compositions of the present invention are particularly intended for the treatment of both T1DM and T2DM, and for the prevention of T2DM in those individuals with pre-diabetes, or impaired glucose tolerance (IGT).

It is found that the present peptide containing compositions can be used for type 2 diabetes or prediabetes, preferably to lower post-prandial glucose concentrations or to increase post-prandial insulin secretion in blood.

The compositions comprising peptide and optionally carbohydrates stimulate insulin secretion and increase glucose disposal to insulin sensitive target tissues such as adipose tissue, skeletal muscle and liver and, thus, provide synergistic effects in the treatment of diabetes mellitus.

It is generally recognised that stress-related diseases, and the negative effects of stress upon the body, have a significant impact upon many people. In recent years the effects of stress, and its contribution towards various the development of various diseases and conditions, has gained wider acceptance in the medical and scientific community. Consumers are now becoming increasingly aware of these potential problems and are becoming increasingly interested in reducing or preventing the possible negative impact of stress on their health.

It is a further object of the invention to provide a food product, or an ingredient which can be incorporated therein, which is suitable for use in helping the body deal with the effects of stress.

It is a further object to provide a food product comprising the present peptide containing composition which provides a health benefit, such as helping the body deal with the negative effects of stress.

The term nutraceutical as used herein denotes the usefulness in both the nutritional and pharmaceutical field of application. Thus, the novel nutraceutical compositions can find use as supplement to food and beverages, and as pharmaceutical formulations or medicaments for enteral or parenteral application which may be solid formulations such as capsules or tablets, or liquid formulations, such as solutions or suspensions. As will be evident from the foregoing, the term nutraceutical composition also comprises food and beverages comprising the present peptide containing composition and optionally carbohydrate as well as supplement compositions, for example dietary supplements, comprising the aforesaid active ingredients.

The term dietary supplement as used herein denotes a product taken by mouth that contains a "dietary ingredient" intended to supplement the diet. The "dietary ingredients" in these products may include: vitamins, minerals, herbs or other botanicals, amino acids, and substances such as enzymes, organ tissues, glandulars, and metabolites. Dietary supplements can also be extracts or concentrates, and may be found in many forms such as tablets, capsules, softgels, gelcaps, liquids, or powders. They can also be in other forms, such as a bar, but if they are, information on the label of the dietary supplement will in general not represent the product as a conventional food or a sole item of a meal or diet.

A multi-vitamin and mineral supplement may be added to the nutraceutical compositions of the present invention to obtain an adequate amount of an essential nutrient missing in some diets. The multi-vitamin and mineral supplement may also be useful for disease prevention and protection against nutritional losses and deficiencies due to lifestyle patterns and common inadequate dietary patterns sometimes observed in diabetes. Moreover, oxidant stress has been implicated in the development of insulin resistance. Reactive oxygen species may impair insulin stimulated glucose uptake by disturbing the insulin receptor signaling cascade. The control of oxidant stress with antioxidants such as α-tocopherol (vitamin E) ascorbic acid (vitamin C) may be of value in the treatment of diabetes. Therefore, the intake of a multi-vitamin supplement may be added to the above mentioned active substances to maintain a well balanced nutrition.

Furthermore, the combination of the present peptide containing composition with minerals such as magnesium ($Mg^{2+}$), Calcium ($Ca^{2+}$) and/or potassium ($K^+$) may be used for the improvement of health and the prevention and/or treatment of diseases including but not limited to cardiovascular diseases and diabetes.

In a preferred aspect of the invention, the nutraceutical composition of the present invention contains the present peptide containing compositions. Both IPP and VPP are suitably is present in the composition according to the invention in an amount to provide a daily dosage from about 0.001 g per kg body weight to about 1 g per kg body weight of the subject to which it is to be administered. A food or beverage suitably contains about 0.05 g per serving to about 50 g per serving of IPP and VPP, respectively. If the nutraceutical composition is a pharmaceutical formulation such formulation may contain IPP and VPP, respectively, in an amount from about 0.001 g to about 1 g per dosage unit, e.g., per capsule or tablet, or from about 0.035 g per daily dose to about 70 g per daily dose of a liquid formulation. The present peptide containing compositions suitably are present in the composition according to the invention in an amount to provide a daily dosage from about 0.01 g per kg body weight to about 3 g per kg body weight of the subject to which it is to be administered. A food or beverage suitably contains about 0.1 g per serving to about 100 g per serving of protein hydrolysates. If the nutraceutical composition is a pharmaceutical formulation such formulation may contain peptide containing compositions in an amount from about 0.01 g to about 5 g per dosage unit, e.g., per capsule or tablet, or from about 0.7 g per daily dose to about 210 g per daily dose of a liquid formulation.

In yet another preferred aspect of the invention a composition comprises the present peptide as specified above and optionally carbohydrates. Carbohydrates suitably are present in the composition according to the invention in an amount to provide a daily dosage from about 0.01 g per kg body weight to about 7 g per kg body weight of the subject to which it is to be administered. A food or beverage suitably contains about 0.5 g per serving to about 200 g per serving of carbohydrates. If the nutraceutical composition is a pharmaceutical formulation such formulation may contain carbohydrates in an amount from about 0.05 g to about 10 g per dosage unit, e.g., per capsule or tablet, or from about 0.7 g per daily dose to about 490 g per daily dose of a liquid formulation.

Dosage Ranges (for a 70 Kg Person)
VPP and IPP: 0.005-70 g/day (each)
Protein hydrolysates: 0.07-210 g/day
Unhydrolysed proteins: 0.07-210 g/day
Carbohydrates: 0.1-490 g/day It is an object of the invention to provide an edible material which can be used to provide health benefits to a subject consuming it. It is yet a further object to provide such an edible material which can conveniently be ingested either in isolated form or incorporated into a food product.

It is a further object of the invention to provide a food product, or an ingredient which can be incorporated therein, which is suitable for use in body weight control programmes.

It is a further object of the invention to provide a food product, or an ingredient which can be incorporated therein, which is suitable for helping to maintain cardiovascular health, e.g. through ACE inhibition.

It is a further object of the invention to provide a food product, or an ingredient which can be incorporated therein, which have acceptable stability and/or organoleptic properties, in particular good taste, such as an absence of or an acceptable level of bitterness.

It is a further object to provide a food product having a high concentration of an ingredient which provides a health benefit, such as aiding the prevention of obesity/body weight control and/or helping maintain cardiovascular health.

Surprisingly, one or more of these objects is attained according to the invention by the use of the present peptide containing composition for the preparation of a food product which provides a health benefit upon consumption.

According to a first aspect the present invention provides the use of the present peptide containing composition for the manufacture of a functional food product for the prevention of obesity or body weight control.

According to a second aspect the present invention provides the use of the present peptide containing composition for the manufacture of a functional food product for cardiovascular health maintenance.

It is especially preferred according to the present invention that cardiovascular health maintenance comprises the inhibition of angiotensin-converting (ACE) enzyme and/or the control of blood glucose levels.

According to a third aspect the present invention provides a functional food product capable of providing a health benefit to the consumer thereof, said health benefit selected from the prevention of obesity, body weight control and cardiovascular health maintenance and comprising the present peptide containing composition.

A further advantage of the peptide containing composition according to the present invention is that this peptide containing composition can be conveniently incorporated into food products, to produce, functional food products, without unacceptably affecting the stability and/or organoleptic properties thereof.

"Health benefit agent(s)" according to the present invention are materials which provide a health benefit, that is which have a positive effect on an aspect of health or which help to maintain an aspect of good health, when ingested, these aspects of good health being prevention of obesity, body weight control and cardiovascular health maintenance. "Health benefit" means having a positive effect on an aspect of health or helping to maintain an aspect of good health.

"Functional food products" according to the present invention are defined as food products (including for the avoidance of doubt, beverages), suitable for human consumption, in which the peptide containing composition of the present invention is used as an ingredient in an effective amount, such that a noticeable health benefit for the consumer of the food product is obtained.

The term "comprising" where used herein is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

WO 02/45524 describes a proline specific protease obtainable from *Aspergillus niger*. The *A. niger* derived enzyme cleaves preferentially at the carboxyterminus of proline, but can also cleave at the carboxyterminus of hydroxyproline and, be it with a lower efficiency, at the carboxyterminus of alanine. WO 02/45524 also teaches that there exists no clear homology between this *A. niger* derived enzyme and the known prolyl oligopeptidases from other microbial or mammalian sources. In contrast with known prolyl oligopeptidases, the *A. niger* enzyme has an acid pH optimum. Although the known prolyl oligopeptidases as well as the *A. niger* derived enzyme are so called serine proteases, we show in Example 1 that the *A. niger* enzyme belongs to a completely different subfamily. The secreted *A. niger* enzyme appears to be a member of family S28 of serine peptidases rather than the S9 family into which most cytosolic prolyl oligopeptidases have been grouped (Rawlings, N. D. and Barrett, A. J.; Biochim. Biophys. Acta 1298 (1996) 1-3). In Example 2 we show the pH and temperature optima of the *A. niger* derived proline specific protease. In Example 3 we demonstrate that the *A. niger* derived enzyme preparation as used in the process of the present invention exhibits a very narrow substrate specificity meaning that no significant endoproteolytic activity other than the endoproteolytic activity inherent to the pure proline specific endoprotease is present. We also demonstrate that our *A. niger* derived enzyme preparation used according to the present invention does not contain any exoproteolytic, more specifically aminopeptidolytic side activities (cf Example 9). In Example 4 of the present application we show that the *Aspergillus* enzyme is not an oligopeptidase but a true endopeptidase able to hydrolyse intact proteins, large peptides as well as smaller peptide molecules without the need of an accessory endoprotease. This new and surprising finding allows us to omit the use of an accessory endoprotease so that hydrolysates with unprecedented high contents of peptides with a carboxyterminal proline residue can be generated. Furthermore the omission of an accessory endoprotease is preferred to achieve an efficient removal of the bulk of the substrate protein. As a result highly concentrated ACE inhibiting peptide mixtures characterized by very high proline contents are obtained. Such new hydrolysates can be prepared from different proteinaceous starting materials be it from vegetable or from animal origin. Examples of such starting materials are whey proteins, whey beta-lactoglobulin, whey alpha lactalbumin, caseins, isolated casein fractions, gelatin, fish or egg proteins, potato protein, wheat and maize gluten, soy and pea protein, rice protein as well as lupin protein. From a substrate like gelatin with a high content of proline as well as hydroyproline, hydrolysates with unprecedented high contents of peptides with either a carboxyterminal proline or hydroxyproline residue can be generated. As the *A. niger* enzyme (like the known prolyl oligopeptidases) enzyme is unable to cleave Pro-Pro or Pro-Hyp, Hyp-Pro or Hyp-Hyp bonds, the approach will also yield hydrolysates containing unprecedented high contents of peptides having two, three or even more carboxyterminal proline or hydroxyproline residues. Obviously the nature and the proline content of the proteinaceous starting material dictates the probability of generating such peptides. Preferred substrates are substrates containing more than 6% proline (i.e. more than 6 grams of this amino acid per 100 gram of protein) such as casein, gelatin, wheat and maize glutens. In view of the fact that peptides carrying such carboxyterminal amino acid sequences can be expected to have a fair chance of surviving the proteolytic activity in the gastrointestinal tract, hydrolysates created by incubation with the *A. niger* derived prolyl endoprotease provide an excellent starting material for the isolation of known biologically active peptides as well as for the identification of new biologically active peptides. As sodium is known to play a role in hypertension, preferred substrates for the production of ACE inhibiting peptides are ammonia, calcium, magnesium and potassium rather than sodium salts of these proteins.

The process according to the present invention hinges on the activity of a proline specific endo activity, be it a proline specific oligopeptidase with a neutral pH optimum or a proline specific endoprotease with an acid pH optimum, in combination with an aminopeptidase activity. The pH optimum of the *A. niger* derived prolyl endoprotease is around 4.3. (see FIG. 1). Because of this low pH optimum incubating bovine milk caseinate with the *A. niger* derived prolyl endoprotease is not self-evident. Bovine milk caseinate will precipitate if the pH drops below 6.0 and at this pH value the *A. niger* enzyme has a limited activity only. Here we show that even under this rather unfavorable condition an incubation with the *A. niger* derived prolyl endoprotease can yield several ACE inhibiting peptides. According to the present invention the ACE inhibiting tripeptides IPP and LPP are produced in yields that correspond with 70% of the amount theoretically present in casein. Quite surprisingly the ACE inhibiting peptide VPP is not produced if the aminopeptidolytic activity is absent. In this case only the VPP precursor VVVPP is produced in a high yield. We also show here that if the aminopeptidolytic activity is present in combination with the proline specific protease VPP is produced in an almost 100% yield. These results are obtained upon incubating the caseinate with the *A. niger* derived endoprotease and an aminopeptidase in a simple one-step enzyme process and under conditions that minimise the chances of a microbial contamination.

Aqueous solutions containing protein are highly susceptible for microbial infections, especially if kept for many hours at pH values above 5.0 and at temperatures of 50 degrees C. or below. Especially microbial toxins that can be produced during such prolonged incubation steps and are likely to survive subsequent heating steps and form a potential threat to food grade processes. Unlike the conditions described in EP 1 231 279 the process according to the present invention preferably uses an incubation temperature above 50 degrees C. In combination with the one-step enzyme process in which the enzyme incubation is carried out for a period less than 24 hours, preferably less than 8 hours, more preferably less than 4 hours, the process according to the invention offers the advantage of an improved microbiological stability.

Bovine milk casein incorporates a number of different proteins including beta-casein and kappa-casein. According to the known amino acid sequences beta-casein encompasses the ACE inhibitory tripeptides IPP, VPP and LPP. Kappa-casein encompasses IPP only. In Example 5 we show that incubating potassium caseinates with the *A. niger* derived prolyl endoprotease generates the known ACE inhibiting peptides IPP as well as LPP in high yields. Using the present enzyme-substrate ratio in combination with the high temperature conditions, the excision of IPP and LPP is completed within a 3 hours incubation period. Quite surprisingly a concomitant production of significant quantities of the tripeptide VPP cannot be demonstrated. The fact that the *A. niger* derived enzyme does not contain significant aminopeptidase activity (cf. Example 9) strongly suggests that the IPP formed is released from the -A107-I108-P109-P110- sequence present in kappa-caseine. Presumably the peptide bond carboxyterminal of IPP is cleaved by the main activity of the *A. niger* derived prolyl endoprotease whereas cleavage of the preceding Ala-Ile bond is accomplished by its Ala-specific side activity.

Therefore the present invention results in a smaller number of water soluble peptides than in the prior art processes. Among these water soluble peptides IPP, VPP an LPP are present in major amounts. This is especially important in case a high concentration of IPP and LPP compounds are needed without many other, often less active compounds.

According to the present process preferably at least 20%, more preferably at least 30%, most preferably at least 40% of an -A-I-P-P-, an -A-L-P-P- or an -A-V-P-P-sequence present in a protein is converted into IPP, LPP or VPP, respectively. Furthermore according to the present process preferably at least 20%, more preferably at least 30%, still more preferably at least 40% and most preferably at least 50% of a -P-L-P-P- or a -P-I-P-P- or a -P-V-P-P- sequence present in the protein is converted into LPP or IPP or VPP, respectively.

Hereinabove is described that preferably an -A- or -P-residue is present in the amino acid sequence of the protein N-terminal of (preceding) an -I-P-P, -V-P-P or -L-P-P sequence.

According to present invention between the -A- or -P- residue and the -I-, -V- or -L-residue, preferably 0 to 5 amino acid residues may be present. Upon hydrolysis, the protein will be cleaved C-terminal of the -A- or -P- residue as well as C-terminal of the -P-P- sequence by the proline specific protease. Subsequently the amino acids preceding the -I-P-P, -V-P-P or the -L-P-P sequence will be removed one by one by the aminopeptidase. Because the aminopeptidase is unable to cleave an I-P, an V-P or an L-P peptide bond, the I-P-P, V-P-P or L-P-P sequences will remain intact.

For example when two amino acids -V-V- are present between -P- and -V-P-P- in the amino acid sequence of casein, first the sequence will be cut after -P- and -P-P- by the proline specific endo protease, and subsequently the two valine (V) residues will be removed by the amino peptidase to result in VPP.

In Example 6 we illustrate the 5-fold purification effect by a new and surprising purification step. In this process the hydrolysate is formed during the brief enzyme incubation period at 55 degrees C., pH 6.0 and is then heated to a temperature above 80 degrees C. to kill all contaminating microorganisms and to inactivate the *A. niger* derived prolyl endopeptidase. Subsequently the hydrolysate is slowly acidified to realise a pH drop to 4.5 or at least below 5.0. At this pH value, which cannot be used to inactivate the *A. niger* derived prolyl endopeptidase because it represents the optimum condition for the enzyme, all large peptides from the caseinate precipitate so that only the smaller peptides remain in solution. Preferably the acidified mixture is kept at a low temperature for several hours to precipitate as much proteins and non-ACE inhibiting peptides as possible. As the precipitated caseinates can be easily removed by decantation or a filtration step or a low speed (i.e. below 5000 rpm) centrifugation, the aqueous phase contains a high proportion of bioactive peptides relative to the amount of protein present. According to Kjeldahl data 80 to 70% of the caseinate protein is removed by the low speed centrifugation step which implies a four- to five-fold purification of the ACE inhibiting peptides. Optionally the purification can be further improved by a subsequent ultrafiltration step. We also have found that this purification principle can be advantageously applied to obtain biologically active peptides obtained from proteinaceous material other than casein. Also proteins that are fermented by suitable microorganisms can be separated and purified according to the present process. Incubating enzyme and substrate at a pH value close to where the substrate will precipitate and where the enzyme is still active, will permit this purification step. Due to the low pH optimum of the *A. niger* derived prolyl endoprotease, substrate precipitations in the range between pH 1.5 to 6.5 can be considered. In view of their specific precipitation behaviour, gluten precipitations above pH 3.5, whey protein precipitations above pH 3.5 and below pH 6.0, egg white precipitations above pH 3.5 and below pH 5.0 form examples of conditions whereby the hydrolysed protein precipitates and the precipitated proteins can be separated from the hydrolysed protein or peptides. This soluble fraction of the hydrolysate is also comprised by the wording hydrolysate. This acid-soluble hydrolysate is formed by the hydrolysis of the protein according to the present followed by amending the acidic conditions so that in soluble hydrolysed parts can be separated from the soluble peptides. This separation can be done for example by sedimentation or centrifugation of the insoluble parts. For a gluten hydrolysate the acidic separation conditions are preferably pH=4, for whey hydrolysate the acidic conditions are preferably pH=4.5, for caseine hydrolysate the acidic conditions are preferably pH=4.5 and for egg white the acidic conditions are preferably pH=5.0. In general the preferred acidic conditions for the separation are pH=4.5.

By hydrolysate is meant the product that is formed by the hydrolysis of the protein (or briefly protein hydrolysate or hydrolysed protein), the acid-soluble hydrolysate being the soluble fraction of the protein hydrolysate which is also described herein as soluble peptide containing composition or composition comprising soluble peptides), or a mixture of a protein hydrolysate and an acid soluble hydrolysate.

In nutraceutical applications and food and beverage applications, hydrolysates of the inventions are advantageously used. A protein hydrolysate, an acid-soluble hydrolysate as well as an mixture thereof can be used in a nutraceutical application, a food application or a beverage. Preferably the acid-soluble hydrolysate is used in a nutraceutical application, a food application or a beverage because of the high content of active peptides present. Although the same principle is used in the cheese making process for separating casein curd from whey proteins, in the cheese making process use is made of aspartic endoproteases (EC 3.4.23) only. This enzyme class incorporates well known cheese making enzymes like chymosin and various pepsins like the mammalian pepsins as well as various microbial pepsins like aspergillopepsins and mucorpepsins. In the present application curd in the cheese making process is defined not to be a hydrolysate. Furthermore as discussed above the purification process according to the present invention is not known for hydrolysates produced by a non-aspartic endoprotease.

The cheese making process or the curd/whey separation process is excluded from the purification process of the present invention, so the present purification process is directed to obtain soluble peptides with the proviso that this process is not part of a cheese making process or a curd/whey separation process.

Despite of the superficial resemblance of this purification step with the process of cheese making, it is completely different. In cheese making curd formation is initiated by either an enzyme step ("renneting") or by an acidification step. However, the renneting process proceeds independent of acidification whereas cheese curd coagulation by acidification proceeds independent of an enzyme.

In an alternative purification method the ACE inhibiting peptides are conveniently and efficiently recovered using a water miscible solvent such as ethanol, acetone, propanol-1, propanol-2, methanol or a mixture thereof. In this approach the protein hydrolysate is preferably carefully mixed with 30-60% (v/v) of a water miscible solvent under selected pH conditions so that the larger proteins precipitate and the small ACE inhibiting peptides remain in solution.

After decantation, filtration or low speed centrifugation to remove the precipitate formed during either the acidification or the solvent addition step, the supernatants containing the biologically active peptides can be recovered. A subsequent evaporation, optionally in combination with an additional filtration step followed by a spray drying step will yield an economical route for obtaining a food grade paste or powder with a high bio-activity and a good water solubility. According to one embodiment of the invention these soluble peptides can be hydrolyzed with an amino peptidase to produce IPP, VPP and LPP containing hydrolysates. Upon the digestion of caseinates by a proline specific protease in combination with an aminopeptidase, a white and odourless powder with a high concentration of ACE inhibiting peptides, which is rich in IPP, VPP and LPP, is obtained. The preparation as obtained has a very high proline content. The very high proline content of this preparation is unexpected as proline is one of the most hydrophobic amino acids.

In Example 7 we demonstrate that at least three different commercial enzyme preparations contain the aminopeptidolytic activities required to transform precursor peptides formed by the proline specific protease from *A. niger* into ACE inhibiting tripeptides. In Example 8 we proof that indeed a combination of the proline specific protease with these commercial enzyme preparations can generate high yields of IPP, VPP and LPP in a single enzyme incubation step. In combination with the acid precipitation step described in Example 6 a highly concentrated mixture of ACE inhibiting peptides is obtained. If appropriately diluted to the right tripeptide concentration, a versatile starting material with an excellent palatability is obtained suitable for endowing all kinds of foods and beverages with ACE inhibiting properties. If required, the concentration of the bioactive ingredients can be further increased by subsequent purification in which use is made of the very hydrophobic character of the peptides IPP, VPP and LPP. Preferred purification methods include nanofiltration, extraction for example with butanol followed by evaporation/precipitation or contacting the acidified hydrolysate as obtained with binders like active carbon or chromatographic resins from the Amberlite XAD range (Rohm). Also butyl-sepharose resins as supplied by Pharmacia can be used. Desorption of the ACE inhibiting peptides from such materials can be done with organic solvents like methanol/ethanol mixtures or with propanol. Furthermore supercritical extraction using $CO_2$ or $N_2O$ can be used to obtain highly purified bioactive peptides. In Example 9 we demonstrate that our *A. niger* derived enzyme preparation used according to the present invention is free from significant levels of contaminating endoproteases and amino- and carboxypeptidase activities. All positively identified proteinase samples mentioned in EP 1 231 279 are complex mixtures of different enzymes exhibiting different proteolytic activities. As these proteinase samples used do not incorporate significant quantities of a proline specific protease, a person skilled in the art will understand that the process described in EP 1 231 279 hinges on the combination of a non-specific endoproteolytic activity with adequate carboxypeptidase and/or aminopeptidase activities. The process of the present invention does not rely on such non-specific endoproteolytic activities or on carboxypeptidase activities. According to the present invention a single proline specific endoprotease with a very narrow substrate specificity is used in combination with an aminopeptidase. The absence of any carboxypeptidase activity implies that the final hydrolysate will have reduced levels of free amino acids. Such low levels of free amino acids are preferred to minimise brothy off-tastes that are easily generated in Maillard reactions during processing steps or during pasteurisation or sterilization processes. Also the proline specific proteolytic activity as used in the process according to the present invention is not present in the complex proteinase samples described in EP 1 231 279. Experimental proof for the notion that this activity is essentially absent in non-recombinant *Aspergillus* strains can be found in WO 02/45524 and in Example 9 of the present application.

The ACE inhibiting peptides as obtained either before or after an additional (for example chromatography) purification step may be used for the incorporation into food products that are widely consumed on a regular basis. Examples of such products are margarines, spreads, various dairy products such as butter or yoghurts or milk or whey containing beverages, preferably yoghurt or milk based products such as yoghurt and milk. Also in other beverages such as fruit drinks or soy drinks, the hydrolysate of the present invention can be used. Another option is the use of the hydrolysate in health products such as fruit bars, protein bars, energy bars, cereal based products for example breakfast cereals. Preferably the food or beverage product or dietary supplement is selected from the group of margarines, spreads, butter, dairy products or whey containing beverages, preferably yoghurt or milk based products such as yoghurt or milk, wherein said food or beverage product or dietary supplement comprises the amounts of protein hydrolysate or the amount of IPP as indicated above.

Especially preferred are food or beverage product or dietary supplements as described here above for use to relief hypertension of human beings. Preferred serving sizes for the food or beverage or dietary supplements are for example 5-350 grams per serving, for example from 5 to 150 grams. Preferably the number of servings per day is 1-10, for example 2 to 5.

Although such compositions are typically administered to human beings, they may also be administered to animals, preferably mammals, to relief hypertension. Furthermore the high concentration of ACE inhibitors in the products as obtained makes these products very useful for the incorporation into dietary supplements in the form off pills, tablets or highly concentrated solutions or pastes or powders. Slow release dietary supplements that will ensure a continuous release of the ACE inhibiting peptides are of particular interest. The ACE inhibiting peptides according to the invention may be formulated as a dry powder in, for example, a pill, a tablet, a granule, a sachet or a capsule. Alternatively the enzymes according to the invention may be formulated as a liquid in, for example, a syrup or a capsule. The compositions used in the various formulations and containing the enzymes according to the invention may also incorporate at least one compound of the group consisting of a physiologically acceptable carrier, adjuvant, excipient, stabiliser, buffer and diluant which terms are used in their ordinary sense to indicate substances that assist in the packaging, delivery, absorption, stabilisation, or, in the case of an adjuvant, enhancing the physiological effect of the enzymes. The relevant background on the various compounds that can be used in combination with the enzymes according to the invention in a powdered form can be found in "Pharmaceutical Dosage Forms", second edition, Volumes 1, 2 and 3, ISBN 0-8247-8044-2 Marcel Dekker, Inc. Although the ACE inhibiting peptides according to the invention formulated as a dry powder can be stored for rather long periods, contact with moisture or humid air should be avoided by choosing suitable packaging such as for example an aluminium blister. A relatively new oral application form is the use of various types of gelatin capsules or gelatin based tablets.

In view of the relevance of natural ACE inhibiting peptides to fight hypertension the present new and cost effective route offers an attractive starting point for mildly hypotensive alimentary or even veterinary products. Because the present route also includes a surprisingly simple purification step, the possibilities for blood pressure lowering concentrated dietary supplements are also enlarged.

The process according to the invention can be accomplished using any proline specific oligo- or endoprotease. By proline specific oligopeptidases according to the invention or used according to the invention are meant the enzymes belonging to EC 3.4.21.26. By the proline specific endo protease according to the invention or used according to the invention is meant the polypeptide as mentioned in claims 1-5, 11 and 13 of WO 02/45524. Therefore this proline specific endo protease is a polypeptide which has proline specific endoproteolytic activity, selected from the group consisting of:

(a) a polypeptide which has an amino acid sequence which has at least 40% amino acid sequence identity with amino acids 1 to 526 of SEQ ID NO:2 or a fragment thereof;

(b) a polypeptide which is encoded by a polynucleotide which hybridizes under low stringency conditions with (i) the nucleic acid sequence of SEQ ID NO:1 or a fragment thereof which is at least 80% or 90% identical over 60, preferably over 100 nucleotides, more preferably at least 90% identical over 200 nucleotides, or (ii) a nucleic acid sequence complementary to the nucleic acid sequence of SEQ ID NO:1. The SEQ ID NO:1 and SEQ ID NO:2 as shown in WO 02/45524. Preferably the polypeptide is in isolated form.

The preferred polypeptide used according to the present invention has an amino acid sequence which has at least 50%, preferably at least 60%, preferably at least 65%, preferably at least 70%, more preferably at least 80%, even more preferably at least 90%, most preferably at least 95%, and even most preferably at least about 97% identity with amino acids 1 to 526 of SEQ ID NO: 2 or comprising the amino acid sequence of SEQ ID NO:2.

Preferably the polypeptide is encoded by a polynucleotide that hybridizes under low stringency conditions, more preferably medium stringency conditions, and most preferably high stringency conditions, with (i) the nucleic acid sequence of SEQ ID NO:1 or a fragment thereof, or (ii) a nucleic acid sequence complementary to the nucleic acid sequence of SEQ ID NO: 1.

The term "capable of hybridizing" means that the target polynucleotide of the invention can hybridize to the nucleic acid used as a probe (for example, the nucleotide sequence set forth in SEQ. ID NO: 1, or a fragment thereof, or the complement of SEQ ID NO: 1) at a level significantly above background. The invention also includes the polynucleotides that encode the proline specific endoprotease of the invention, as well as nucleotide sequences which are complementary thereto. The nucleotide sequence may be RNA or DNA, including genomic DNA, synthetic DNA or cDNA. Preferably, the nucleotide sequence is DNA and most preferably, a genomic DNA sequence. Typically, a polynucleotide of the invention comprises a contiguous sequence of nucleotides which is capable of hybridizing under selective conditions to the coding sequence or the complement of the coding sequence of SEQ ID NO: 1. Such nucleotides can be synthesized according to methods well known in the art.

A polynucleotide of the invention can hybridize to the coding sequence or the complement of the coding sequence of SEQ ID NO:1 at a level significantly above background. Background hybridization may occur, for example, because of other cDNAs present in a cDNA library. The signal level generated by the interaction between a polynucleotide of the invention and the coding sequence or complement of the coding sequence of SEQ ID NO: 1 is typically at least 10 fold, preferably at least 20 fold, more preferably at least 50 fold, and even more preferably at least 100 fold, as intense as interactions between other polynucleotides and the coding sequence of SEQ ID NO: 1. The intensity of interaction may be measured, for example, by radiolabelling the probe, for example with 32P. Selective hybridization may typically be achieved using conditions of low stringency (0.3M sodium chloride and 0.03M sodium citrate at about 40° C.), medium stringency (for example, 0.3M sodium chloride and 0.03M sodium citrate at about 50° C.) or high stringency (for example, 0.3M sodium chloride and 0.03M sodium citrate at about 60° C.).

The UWGCG Package provides the BESTFIT program which may be used to calculate identity (for example used on its default settings).

The PILEUP and BLAST N algorithms can also be used to calculate sequence identity or to line up sequences (such as identifying equivalent or corresponding sequences, for example on their default settings).

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold. These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix alignments (B) of 50, expectation (E) of 10, M=5, N=4, and a comparison of both strands.

The BLAST algorithm performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The strains of the genus *Aspergillus* have a food grade status and enzymes derived from these micro-organisms are known to be from an unsuspect food grade source. According to another preferred embodiment, the enzyme is secreted by its producing cell rather than a non-secreted, so called cytosolic enzyme. In this way enzymes can be recovered from the cell broth in an essentially pure state without expensive puri-

MATERIALS AND METHODS

Figure 1:
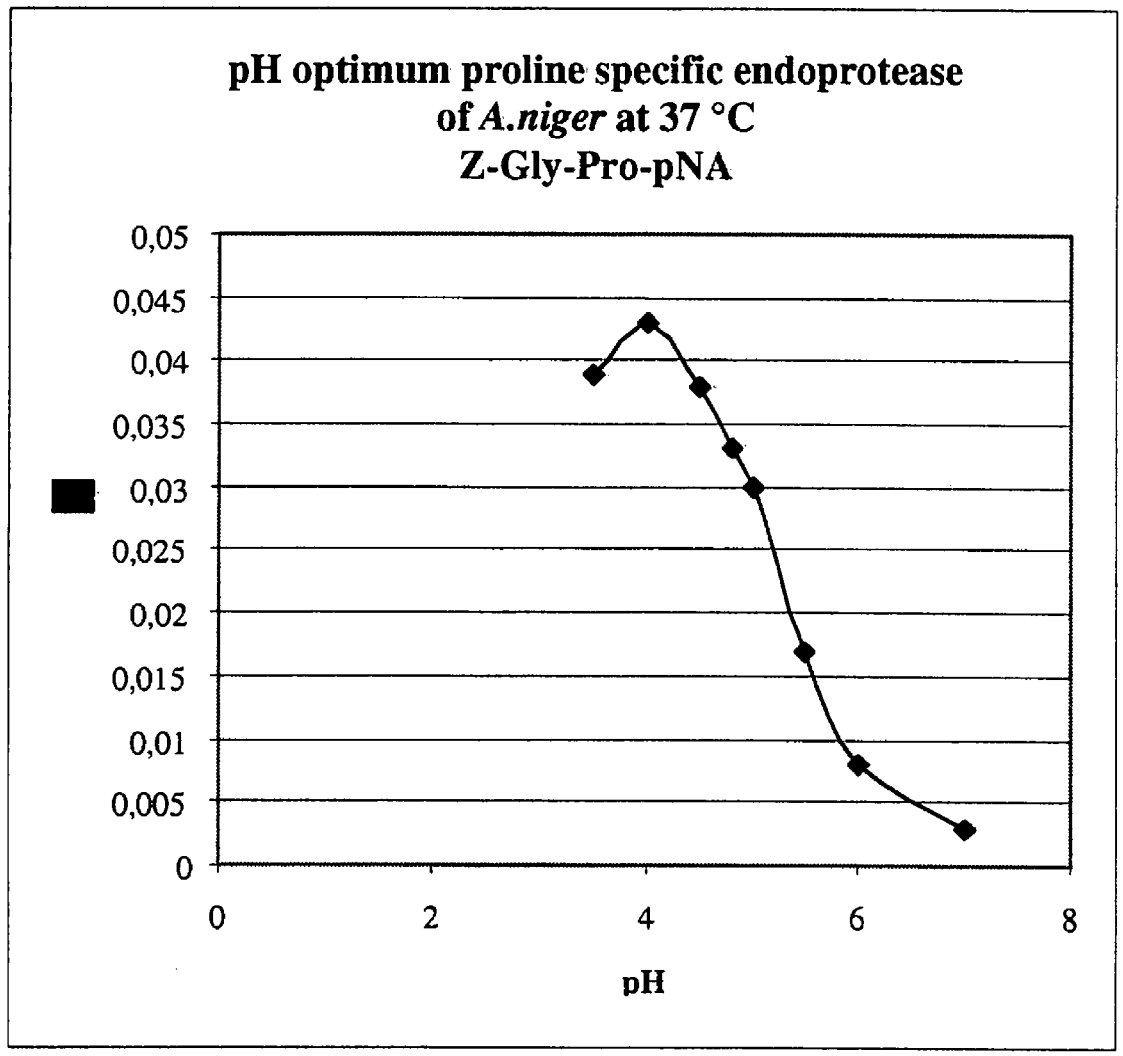
FIG. 1: A graphic representation of the pH optimum of the *A. niger* derived prolyl endoprotease

Edible sodium and potassium caseinate spray (88%) was obtained from DMV International, The Netherlands. Synthetic chromogenic peptides were obtained from either Pepscan Systems B.V. The Netherlands or from Bachem, Switzerland. Flavourzyme 1000L Batch HPN00218 was obtained from Novozymes (Denmark), Sumizyme FP from Shin Nihon (Japan) and Corolase LAP Ch.: 4123 from AB Enzymes (UK).

Proline-Specific Endoprotease from *A. niger.*

Overproduction of the proline specific endoprotease from *Aspergillus niger* was accomplished as described in WO 02/45524. The activity of the enzyme was tested on the synthetic peptide Z-Gly-Pro-pNA at 37 degrees C. in a citrate/disodium phosphate buffer pH 4.6. The reaction product was monitored spectrophotometrically at 405 nM. A unit is defined as the quantity of enzyme that liberates 1 μmol of p-nitroanilide per minute under these test conditions.

Chromatographic Purification of the *A. niger* Derived Endoprotease

The culture broth obtained from an overproducting *A. niger* strain was used for chromatographic purification of the protease to remove any contaminating endo- and exoproteolytic activities. To that end the fermentation broth was first centrifuged to remove the bulk of the fungal mass and the supernatant was then passed through a number of filters with decreasing pore sizes to remove all cell fragments. Finally, the ultrafiltrate obtained was diluted ten times in 20 millimole/liter sodium acetate pH 5.1 and applied on a Q-Sepharose FF column. Proteins were eluted in a gradient from 0 to 0.4 moles/liter NaCl in 20 millimole/liter sodium acetate pH 5.1. Peak fractions displaying activity towards the cleavage of Z-Gly-Pro-pNA were collected and pooled, according to the protocol described in World Journal of Microbiology & Biotechnology 11, 209-212 (1995), but under slightly modified assay conditions. Taking the acid pH optimum of the *A. niger* derived proline-specific endoprotease into account, the enzyme assay was carried out at pH 4.6 in a citrate/diphosphate buffer at 37° C. Pooling of the active fractions followed by concentration finally yielded a preparation which showed only a single band on SDS-PAGE and one peak on HP-SEC. Further analysis by hydrophobic interaction chromatography confirmed the purity of the enzyme preparation obtained.

Degree of Hydrolysis

The Degree of Hydrolysis (DH) as obtained during incubation with the various protolytic mixtures was monitored using a rapid OPA test (Nielsen, P.M.; Petersen, D.; Dambmann, C. Improved method for determining food protein degree of hydrolysis. *Journal of Food Science* 2001, 66, 642-646).

Kjeldahl Nitrogen

Total Kjeldahl Nitrogen was measured by Flow Injection Analysis. Using a Tecator FIASTAR 5000 Flow Injection System equipped with a TKN Method Cassette 5000-040, a Pentium 4 computer with SOFIA software and a Tecator 5027 Autosampler the ammonia released from protein containing solutions was quantitated at 590 nm. A sample amount corresponding with the dynamic range of the method (0.5-20 mg N/l) is placed in the digestion tube together with 95-97% sulphuric acid and a Kjeltab subjected to a digestion program of 30 minutes at 200 degrees C. followed by 90 minutes at 360 degrees C. After injection in the FIASTAR 5000 system the nitrogen peak is measured from which the amount of protein measured can be inferred.

Amino Acid Analysis

A precisely weighed sample of the proteinaceous material was dissolved in dilute acid and precipitates were removed by centrifugation in an Eppendorf centrifuge. Amino acid analysis was carried out on the clear supernatant according to the PicoTag method as specified in the operators manual of the Amino Acid Analysis System of Waters (Milford Mass., USA). To that end a suitable sample was obtained from the liquid, then dried and subjected to vapour phase acid hydrolysis and derivatised using phenylisothiocyanate. The various derivatised amino acids present were quantitated using HPLC methods and added up to calculate the total level of free amino acids in the weighed sample. The amino acids Cys and Trp are not included in the data obtained in this analysis.

LC/MS/MS Analysis

HPLC using an ion trap mass spectrometer (Thermoquest®, Breda, the Netherlands) coupled to a P4000 pump (Thermoquest®, Breda, the Netherlands) was used in quantification of the peptides of interest, among these the tripeptides IPP, LPP and VPP, in the enzymatic protein hydrolysates produced by the inventive enzyme mixture. The peptides formed were separated using a Inertsil 3 ODS 3, 3 mm, 150*2.1 mm (Varian Belgium, Belgium) column in combination with a gradient of 0.1% formic acid in Milli Q water (Millipore, Bedford, Mass., USA; Solution A) and 0.1% formic acid in acetonitrile (Solution B) for elution. The gradient started at 100% of Solution A, kept here for 5 minutes, increasing linear to 5% B in 10 minutes, followed by linear increasing to 45% of solution B in 30 minutes and immediately going to the beginning conditions, and kept here 15 minutes for stabilization. The injection volume used was 50 microliters, the flow rate was 200 microliter per minute and the column temperature was maintained at 55° C. The protein concentration of the injected sample was approx. 50 micrograms/milliliter.

Detailed information on the individual peptides was obtained by using dedicated MS/MS for the peptides of interest, using optimal collision energy of about 30%. Quantification of the individual peptides was performed using external calibration, by using the most abundant fragment ions observed in MS/MS mode.

The tripeptide LPP (M=325.2) was used to tune for optimal sensitivity in MS mode and for optimal fragmentation in MS/MS mode, performing constant infusion of 5 mg/ml, resulting in a protonated molecule in MS mode, and an optimal collision energy of about 30% in MS/MS mode, generating a B- and Y-ion series.

Prior to LC/MS/MS the enzymatic protein hydrolysates were centrifuged at ambient temperature and 13000 rpm for 10 minutes, filtered through a 0.22 µm filter and the supernatant was diluted 1:100 with MilliQ water.

Nutraceutical Products

The nutraceutical products according to the invention may be of any food type. They may comprise common food ingredients in addition to the food product, such as flavour, sugar, fruits, minerals, vitamins, stabilisers, thickeners, etc. in appropriate amounts.

Preferably, the nutraceutical product comprises 50-200 mmol/kg K$^+$ and/or 15-60 mmol/kg Ca$^{2+}$ and/or 6-25 mmol/kg Mg$^{2+}$ more preferably, 100-150 mmol/kg K$^+$ and/or 30-50 mmol/kg Ca$^{2+}$ and/or 10-25 mmol/kg Mg$^{2+}$ and most preferably 110-135 mmol/kg K$^+$ and/or 35-45 mmol/kg Ca$^{2+}$ and/or 13-20 mmol/kg Mg$^{2+}$. These cations have a beneficial effect of further lowering blood pressure when incorporated in the nutraceutical products according to the invention.

Advantageously the nutraceutical product comprises one or more B-vitamins.

The B-vitamin folic acid is known to participate in the metabolism of homocysteine, an amino acid in the human diet. For a number of years, high homocysteine levels have been correlated to high incidence of cardiovascular disease. It is thought that lowering homocysteine may reduce the risk of cardiovascular disease.

Vitamins B6 and B12 are known to interfere with the biosynthesis of purine and thiamine, to participate in the synthesis of the methyl group in the process of homocysteine methylation for producing methionine and in several growth processes. Vitamin B6 (pyridoxine hydrochloride) is a known vitamin supplement. Vitamin B12 (cyanobalamin) contributes to the health of the nervous system and is involved in the production of red blood cells. It is also known as a vitamin in food supplements.

Because of their combined positive effect on cardiovascular disease risk reduction, it is preferred that products according to the invention comprises vitamin B6 and vitamin B12 and folic acid.

The amount of the B-vitamins in the nutraceutical product may be calculated by the skilled person based daily amounts of these B-vitamins given herein: Folic acid: 200-800 µg/day, preferably 200-400 µg/day; Vitamin B6: 0.2-2 mg/day, preferably 05-1 mg/day and Vitamin B12: 0.5-4 µg/day, preferably 1-2 µg/day.

Preferably, the nutraceutical product comprises from 3 to 25 wt % sterol, more preferred from 7 to 15 wt % sterol. The advantage of the incorporation of sterol is that it will cause reduction of the level of LDL-cholesterol in human blood, which will result in reduction of cardiovascular risk.

Where reference is made to sterol this includes the saturated stanols and esterified derivatives of sterol/stanol or mixtures of any of these.

In this application where reference is made to sterolester, this also includes their saturated derivatives, the stanol esters, and combinations of sterol- and stanol esters.

Sterols or phytosterols, also known as plant sterols or vegetable sterols can be classified in three groups, 4-desmethylsterols, 4-monomethylsterols and 4,4'-dimethylsterols. In oils they mainly exist as free sterols and sterol esters of fatty acids although sterol glucosides and acylated sterol glucosides are also present. There are three major phytosterols namely beta-sitosterol, stigmasterol and campesterol. Schematic drawings of the components meant are as given in "Influence of Processing on Sterols of Edible Vegetable Oils", S. P. Kochhar; Prog. Lipid Res. 22: pp. 161-188.

The respective 5 alpha-saturated derivatives such as sitostanol, campestanol and ergostanol and their derivatives are in this specification referred to as stanols. Preferably the (optionally esterified) sterol or stanol is selected from the group comprising fatty acid ester of β-sitosterol, β-sitostanol, campesterol, campestanol, stigmasterol, brassicasterol, brassicastanol or a mixture thereof.

The sterols or stanols are optionally at least partly esterified with a fatty acid. Preferably the sterols or stanols are esterified with one or more $C_{2-22}$ fatty acids. For the purpose of the invention the term $C_{2-22}$ fatty acid refers to any molecule comprising a $C_{2-22}$ main chain and at least one acid group. Although not preferred within the present context the $C_{2-22}$ main chain may be partially substituted or side chains may be present. Preferably, however the $C_{2-22}$ fatty acids are linear molecules comprising one or two acid group(s) as end group(s). Most preferred are linear $C_{8-22}$ fatty acids as these occur in natural oils.

Suitable examples of any such fatty acids are acetic acid, propionic acid, butyric acid, caproic acid, caprylic acid, capric acid. Other suitable acids are for example citric acid, lactic acid, oxalic acid and maleic acid. Most preferred are myristic acid, lauric acid, palmitic acid, stearic acid, arachidic acid, behenic acid, oleic acid, cetoleic acid, erucic acid, elaidic acid, linoleic acid and linolenic acid.

When desired a mixture of fatty acids may be used for esterification of the sterols or stanols. For example, it is possible to use a naturally occurring fat or oil as a source of the fatty acid and to carry out the esterification via an interesterification reaction.

The above described nutraceutical ingredients, contributing to increasing cardiovascular health, K+, Ca2+ and Mg2+, B-vitamins (folic acid, B6, B12) and sterols are herein collectively referred to as heart health ingredients.

Example 1

The Enzyme as Obtained from *A. niger* Represents a New Class of Proline Specific Enzymes From the entire coding sequence of the *A. niger* derived proline specific endoprotease as provided in WO 02/45524 a protein sequence of 526 amino acids can be determined. The novelty of the enzyme was confirmed by BLAST searches of databases such as SwissProt, PIR and trEMBL. To our surprise, no clear homology could be detected between the *A. niger* enzyme and the known prolyl oligopeptidases. Closer inspection of the amino acid sequence, however, revealed low but significant homology to Pro-X carboxypeptidases (EC3.4.16.2), dipeptidyl aminopeptidases I (EC3.4.14.2), and thymus specific serine protease. All of these enzymes have been assigned to family S28 of clan SC of serine peptidases (*Handbook of Proteolytic Enzymes*; Barrett A. J.; Rawlings N. D.; Woessner J. F., Eds.; Academic Press, London, UK, 1998, 369-415). Also the GxSYxG configuration around the active site serine is conserved between these enzymes and the *A. niger* derived endoprotease. Additionally, members of family S28 have an acidic pH optimum, have specificity for cleaving at the carboxy-terminal side of proline residues and are synthesized with a signal sequence and propeptide just like the *A. niger* derived proline specific endoprotease. Also the size of the *A. niger* enzyme is similar to those the members of family S28. Therefore, the *A. niger* proline specific endoprotease appears to be a member of family S28 of serine proteases rather than the S9 family into which most cytosolic prolyl oligopeptidases including the enzyme obtained from *Flavobacterium meningosepticum* have been grouped. On the basis of these structural and physiological features we have concluded that the *A. niger* enzyme belongs to the S28 rather than the S9 family of serine proteases. An additional feature that discriminates the *A. niger* derived enzyme from the prolyl oligopeptidases belonging to the S9 family is the fact that, unlike the cytosolic prolyl endoproteases belonging to the latter family, the newly identified *A. niger* enzyme is secreted into the growth medium. This is the first report on the isolation and characterization of a member of family S28 from a lower eukaryote.

Example 2

The pH and Temperature Optima of the Proline Specific Endoprotease as Obtained from *A. niger*

To establish the pH optimum of the *A. niger* derived proline specific endoprotease, buffers with different pH values were prepared. Buffers of pH 4.0-4.5-4.8-5.0-5.5 and 6.0 were made using 0.05 mol/l Na-acetate and 0.02 M CaCl2; buffers of pH 7.0 and 8.0 were made using 0.05 M Tris/HCl buffers containing 0.02 M CaCl2. The pH values were adjusted using acetic acid and HCl respectively. The chromogenic synthetic peptide Z-Gly-Pro-pNA was used as the substrate. The buffer solution, the substrate solution and the prolyl endoprotease pre-dilution (in an activity of 0.1 U/mL), were heated to exactly 37.0° C. in a waterbath. After mixing the reaction was followed spectrophotometrically at 405 nm at 37.0° C. for 3.5 min, measuring every 0.5 min. From the results shown in FIG. 1 it is clear that the *A. niger* derived proline specific endoprotease has a pH optimum around 4.

Also the temperature optimum of the prolyl endoprotease was established. To that end the purified enzyme preparation was incubated in 0.1 mol/l Na-acetate containing 0.02 mol/l CaCl2 at pH 5.0 for 2 hours at different temperatures using Caseine Resorufine (Roche Diagnostics, Almere, The Netherlands version 3) as the substrate and enzyme activity was quantified by measuring at 574 nm. According to the results obtained the proline specific endoprotease from *A. niger* has a temperature optimum around 50 degrees C.

Example 3

The Specificity of the *A. niger* Derived Proline Specific Endoprotease

Crude as well as chromatographically purified enzyme samples as obtained from an *A. niger* strain containing multiple copies of the expression cassette (cf WO 02/45524) were tested against a collection of chromogenic peptide substrates to establish the specificity of the encoded endoprotease. The endoproteolytic activity of the enzyme was tested on an AAXpNA substrate. The "pNA" (p-Nitroanilide) substrates cause color changes if the X-pNA peptide bond is cleaved; "X" represents different natural amino acid residues.

Figure 2:
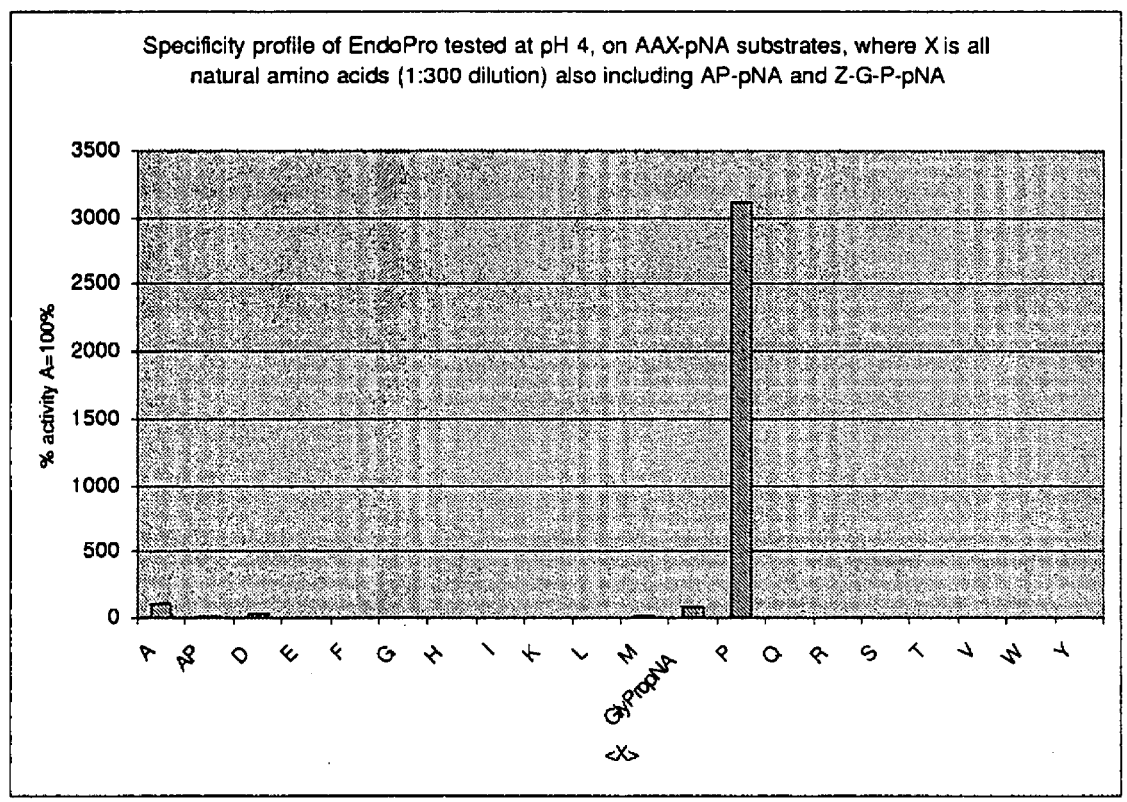
FIG. 2: Specificity profile of the *A. niger* derived prolyl endoprotease

Stock solutions of AAX-pNA substrates (150 mmol/l) were diluted 100× in 0.1M acetate buffer pH 4.0 containing 20 CaCl2. The 10 minutes kinetic measurements at 40 degrees C. in a TECAN Genios MTP Reader (Salzburg, Vienna) at 405 nm recorded the increases in optical density that via data processing in Excel yielded the picture shown in FIG. 2. From the result it is clear that the *A. niger* derived endoprotease is highly specific for prolyl peptide bonds with a side activity towards alanyl bonds. Crude and chromatographically purified preparations showed similar activity profiles. The contamination of the *A. niger* derived endoprotease with aminopeptidases, carboxypeptidases or non-proline specific endoproteases could be shown to be insignificant (see Example 9)

Example 4

The *A. niger* Derived Proline Specific Endoprotease can Hydrolyse Large Proteins as Well as Small Peptides and is Thus a True Endoprotease Owing to a specific structural feature, prolyl oligopeptidases belonging to the S9 family cannot digest peptides larger than 30 amino acids. This limitation is an obvious disadvantage for an enzyme, which is meant to hydrolyse as quickly and as efficiently as possible different proteins. To see if the *A. niger* derived proline specific endoprotease exhibits the same limitations with respect to the size of the substrate molecule, we have incubated the chromatographically purified prolyl endopeptidase from *A. niger* with a small synthetic peptide and with the large ovalbumine molecule and have analysed the hydrolysis products formed by SDS-PAGE.

The synthetic peptide used was a 27-mer of the sequence NH2-FRASDNDRVIDPGKVETLTIRRLHIPR-COOH and was a gift of the Pepscan company (Lelystad, The Netherlands). As shown by its amino acid sequence, this peptide contains 2 proline residues, one in the middle and one near the carboxy terminal end of the peptide.

The intact ovalbumine molecule (Pierce Imject, vials containing 20 mg freeze dried material) consists of 385 amino acids with a molecular weight of 42 750 Da. This molecule contains 14 proline residues, one of which is located at the ultimate C-terminal end of the molecule and cannot be cleaved by a proline specific endoprotease.

Ovalbumin and the oligopeptide were separately incubated at 50° C. with the purified *A. niger* derived proline specific endoprotease. At several time intervals samples were taken which were then analysed using SDS-PAGE.

A chromatographically purified *A. niger* derived proline specific endoprotease with an activity of 4.5 units/ml was diluted 100-fold with 0.1 M acetate buffer pH 4 containing 20 mM CaCl2. The ovalbumine was dissolved in acetate buffer pH 4 to a concentration of 1 mg/ml (22 µM). The 27-mer was dissolved in the same buffer to reach a concentration of 0.48 mg/ml (152 µM). The molarity of the ovalbumine and the 27-mer solution was chosen in such a way that both solutions contained the same molarity in cleavable proline residues. Ovalbumine contains 13 potential proline cleavage sites, whereas the 27-mer peptide has only two. Of both substrate solutions 0.5 ml was incubated with 10 µl (0.45 milliU) of the enzyme solution in an Eppendorf thermomixer at 50° C. At several time intervals 10 µl samples were withdrawn from the incubation mixture and kept at 20° C. until SDS-PAGE. All materials used for SDS-PAGE and staining were purchased from Invitrogen. Samples were prepared using SDS buffer according to manufacturers instructions and separated on 12% Bis-Tris gels using MES-SDS buffer system according to manufacturers instructions. Staining was performed using Simply Blue Safe Stain (Collodial Coomassie G250).

Figure 3:
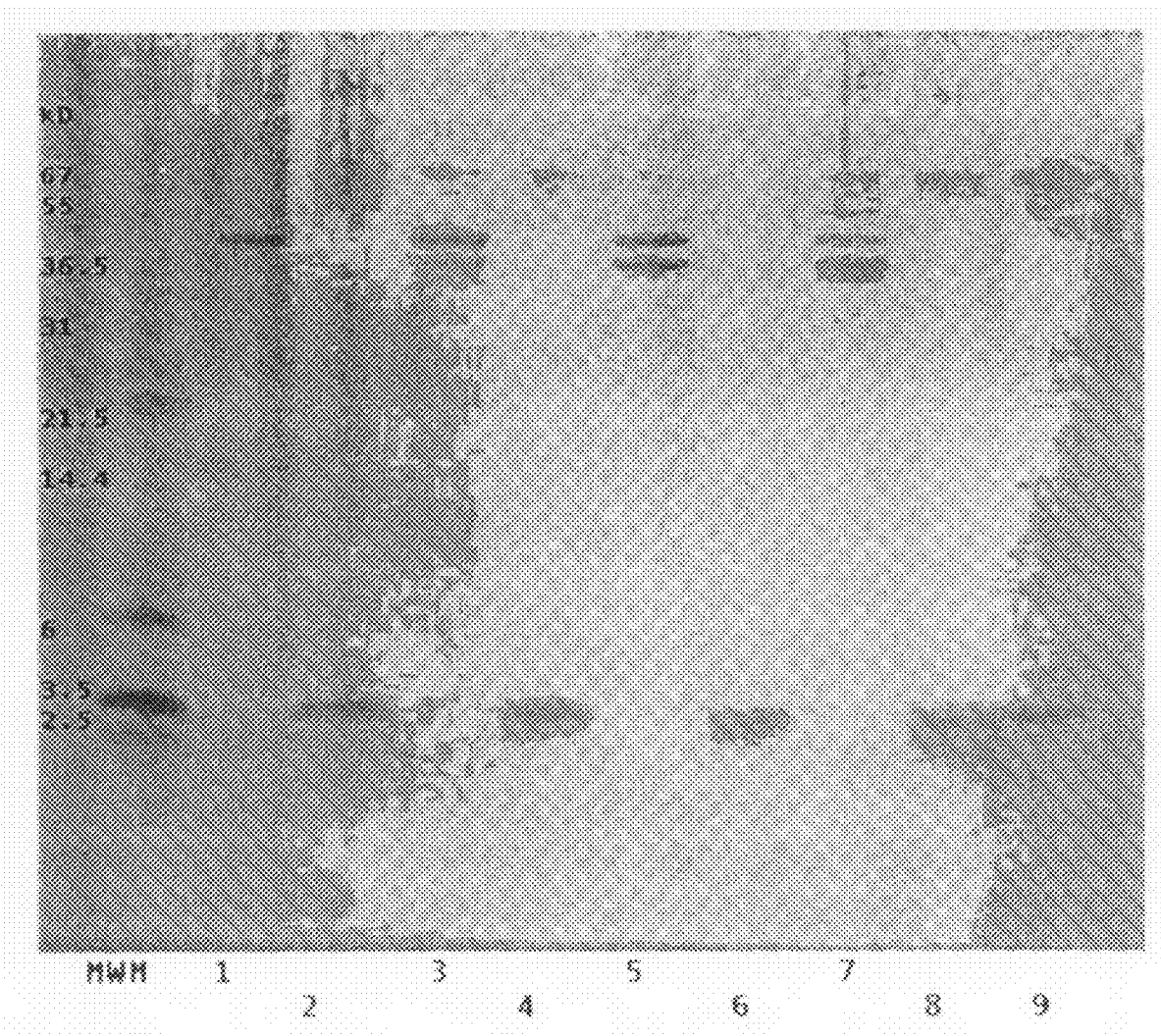
FIG. 3: SDS-PAGE of intact ovalbumine and a synthetic 27-mer peptide after incubation with chromatographically purified *A. niger* derived proline specific endoprotease.

As can be seen in FIG. 3 ovalbumine is cleaved by the *Aspergillus* derived enzyme into a discrete band of about 35 to 36 kD in the first 4.75 hours of incubation (lane 3). Prolonged incubation periods result in further breakdown to smaller products of various molecular weights (lane 7).

The 27-mer peptide is also broken down, as judged by the more faint bands in lanes 4, 6 and 8 as compared to lane 2. The very small molecular weight shift of the product (compare lanes 9 and 8) is most likely due to cleaving of the arginine residue at the carboxylic end of the peptide. The difference is about 200 D (measured using AlphaImager 3.3d software on an AlphaImager 2000 system) and arginine has a MW of 174. This small molecular weight shift is probably the first step in the breakdown of the peptide.

The further decay of the product can only be seen by the decrease in intensity of the band on the SDS gel. The products of further decay are not visible, as in gel staining of components with a MW of about 1000 is not possible with Coomassie Brillant Blue. From this experiment it can be concluded that, unlike the known prolyl oligopeptidases belonging to the S9 family, the *A. niger* derived proline specific endoprotease has no specific preference for cleaving small sized peptides over much larger proteins. As such the *A. niger* derived enzyme represents a true endoprotease and a preferred enzyme to hydrolyse different types of proteins. This finding led to the surprising use of the enzyme as illustrated in the following Example.

Example 5

Incubating Potassium Caseinate with the Proline Specific Endoprotease from *A. niger* Quickly Yields IPP and LPP but no VPP In this experiment we take advantage of the observation made in Example 4 that the proline specific protease as obtained from *A. niger* is a true endoprotease. The overproduced and essentially pure proline specific endoprotease from *A. niger* was incubated with potassium caseinate to test the liberation of the ACE inhibiting peptides IPP, VPP as well as LPP. No other enzyme than the proline specific endoprotease was used in this incubation. As demonstrated in Example 9, the proline specific endoprotease used is free from contaminating endoproteases, aminopeptidases or carboxypeptidases. To limit sodium intake as the result of the ingestion of ACE inhibiting peptides as much as possible, potassium caseinate was used as the substrate in this incubation.

The caseinate was suspended in water of 65 degrees C. in a concentration of 10% (w/w) protein after which the pH was adjusted to 6.0 (measured at 20° C.) using phosphoric acid. Then the temperature of the suspension was brought to 55 degrees C. and the *A. niger* derived proline specific endoprotease was added in a concentration of 4 units/gram of protein (see Materials & Methods section for unit definition). Under continuous stirring this mixture was incubated for 24 hours. No further pH adjustments were carried out during this period. Samples were taken after 1, 2, 3, 4, 8 and 24 hours of incubation. Of each sample enzyme activity was terminated by immediate heating of the sample to 90 degrees C. for 5 minutes. After cooling down the pH of each sample was quickly lowered to 4.5 using phosphoric acid after which the suspension was centrifuged for 5 minutes at 3000 rpm in a Hereaus table top centrifuge. The completely clear supernatant was used for LC/MS/MS analysis to quantify the peptides VPP, IPP, LPP, VVVPP and VVVPPF in the supernatant (see Materials & Methods section).

Bovine milk casein incorporates a number of different proteins including beta-casein and kappa-casein. According to the known amino sequences beta-casein encompasses the ACE inhibitory tripeptides IPP, VPP and LPP. In beta-casein IPP is contained in the sequence $-P_{71}-Q_{72}-N_{73}-I_{74}-P_{75}-P_{76}-$, VPP is contained in the sequence $-P_{81}-V_{82}-V_{83}-V_{84}-P_{85}-P_{86}-$ and LPP is contained in the sequence $-P_{150}-L_{151}-P_{152}-P_{153}-$. Kappa-casein, which is present in acid precipitated caseinate preparations in a molar concentration of less than 50% of the beta-casein concentration, encompasses IPP only. In kappa-casein IPP is contained in the sequence $-A_{107}-I_{108}-P_{109}-P_{110}-$. The other protein constituents of casein do not contain either IPP, VPP or LPP.

Tables 1 and 2 show the concentrations of the peptides present in the acidified and centrifuged supernatants as determined in LC/MS experiments and calculated per gram of potassium caseinate added to the incubation mixture. As shown in Table 1, IPP reaches its maximal concentration after 1 hour of incubation. Beyond that the IPP concentration does not increase any further. The formation of the pentapeptide VVVPP shows the same kinetics as the generation of IPP. As theoretically expected, the molar yield of VVVPP is similar to the molar yield of the LPP peptide. The yield of both LPP and VVVPP reach almost 60% of what would be theoretically feasible. The fact that the maximum concentration of LPP is reached only after 3 hours of incubation suggests that cleavage of that particular part of the beta-caseine molecule is perhaps somewhat more difficult. In contrast with VVVPP, the hexapeptide VVVPPF is not formed at all. This observation suggests that the proline specific endoprotease efficiently cleaves the -P-F- bond hereby generating VVVPP. The tripeptide IPP is formed immediately but its molar yield is not more than about a third of the maximal molar yield of either VVVPP or LPP. As the IPP tripeptide is contained in both beta-caseine as in kappa-caseine, this outcome is unexpected. A likely explanation for this observation is that the proline specific protease can generate IPP but from the kappa-caseine moiety of the caseinates only. In view of the relevant amino acid sequence of kappa-caseine this suggests that the $-A_{107}-I_{108}-$ peptide bond is cleaved by the alanine-specific activity of the enzyme. According to this hypothesis beta-casein digestion with the proline specific endoprotease will yield $Q_{72}-N_{73}-I_{74}-P_{75}-P_{76}$ but not $I_{74}-P_{75}-P_{76}$. The amount of IPP liberated reaches approximately 40% of the quantity that is present in kappa-casein, but not more than about 10% of the IPP that is theoretically present in beta plus kappa casein. This cleavage mechanism for the release of IPP also explains why VPP cannot be formed from its precursor molecule VVVPP: the required endoproteolytic activity is simply not present within the *A. niger* derived enzyme preparation used.

TABLE 1

Molar peptide contents of acidified supernatants obtained upon hydrolysis of potassium caseinate and calculated per gram of protein added.

| micromole/gram protein | IPP | LPP | VPP | VVVPP | VVVPPF |
| --- | --- | --- | --- | --- | --- |
| 1 hr incubation | 2.8 | 4.2 | <0.2 | 8.4 | <0.2 |
| 2 hrs incubation | 2.6 | 6.1 | <0.2 | 9.1 | <0.2 |
| 3 hrs incubation | 2.6 | 8.4 | <0.2 | 9.1 | <0.2 |
| 4 hrs incubation | 2.3 | 8.0 | <0.2 | 8.3 | <0.2 |
| 8 hrs incubation | 2.1 | 9.4 | <0.2 | 7.2 | <0.2 |
| 24 hrs incubation | 2.0 | 9.5 | 0.4 | 5.5 | <0.2 |

TABLE 2

Peptide concentrations in acidified supernatants obtained upon hydrolysis of potassium caseinate and calculated in mg/g protein added.

| milligram/gram protein | IPP | LPP | VPP | VVVPP | VVVPPF |
| --- | --- | --- | --- | --- | --- |
| 1 hr incubation | 0.9 | 1.4 | <0.05 | 4.3 | <0.05 |
| 2 hrs incubation | 0.8 | 2.0 | <0.05 | 4.6 | <0.05 |

TABLE 2-continued

Peptide concentrations in acidified supernatants obtained upon hydrolysis of potassium caseinate and calculated in mg/g protein added.

| milligram/gram protein | IPP | LPP | VPP | VVVPP | VVVPPF |
|---|---|---|---|---|---|
| 3 hrs incubation | 0.8 | 2.7 | <0.05 | 4.6 | <0.05 |
| 4 hrs incubation | 0.8 | 2.6 | <0.05 | 4.2 | <0.05 |
| 8 hrs incubation | 0.7 | 3.0 | <0.05 | 3.6 | <0.05 |
| 24 hrs incubation | 0.7 | 3.1 | 0.1 | 2.8 | <0.05 |

Example 6

Incorporation of an Acid Casein Precipitation Step Results in an Acid-Soluble Proline-Rich Peptide Fraction Exhibiting a 5-Fold Concentration of ACE Inhibiting Peptides In Example 5 we described how potassium caseinate in a concentration of 10% (w/w) protein was subjected to an incubation with the *A. niger* derived proline specific endoprotease at pH 6.0. After various incubation periods samples were heated to stop further enzyme activity after which the pH was lowered to 4.5 to minimise casein solubility. Non soluble casein molecules were removed by a low speed centrifugation. In Tables 1 and 2 we provided concentrations of ACE inhibiting peptides calculated on the basis of the starting concentration of 10% protein. However, as the result of the acidification and the subsequent centrifugation step, a large proportion of the protein added has been removed. To quantitate these reduced protein contents of the acidified supernatants, nitrogen (Kjeldahl) analyses were carried out. According to the latter data the various supernatants were found to contain the following protein levels.

TABLE 3

Protein contents of acidified supernatants

| Sample | Protein content (grams/liter) |
|---|---|
| 1 hr incubation | 21 |
| 2 hrs incubation | 27 |
| 3 hrs incubation | 30 |
| 4 hrs incubation | 34 |
| 8 hrs incubation | 40 |
| 24 hrs incubation | 48 |

Taking these data into account, we recalculated the concentration of the ACE inhibiting peptides present in each supernatant but this time using their actual protein contents. These recalculated data are shown in Table 4.

TABLE 4

Peptide concentrations in acidified supernatants calculated per gram of protein present in the supernatant.

| milligram/gram protein | VPP | IPP | LPP | VVVPP | VVVPPF |
|---|---|---|---|---|---|
| 1 hr incubation | 0.1 | 4.8 | 7.1 | 22.5 | <0.05 |
| 2 hr incubation | 0.1 | 3.4 | 8.0 | 18.9 | <0.05 |
| 3 hr incubation | 0.1 | 3.1 | 10.0 | 17.0 | <0.05 |
| 4 hr incubation | 0.1 | 2.4 | 8.5 | 13.7 | <0.05 |
| 8 hr incubation | 0.1 | 1.9 | 8.4 | 10.0 | <0.05 |
| 24 hr incubation | 0.3 | 1.5 | 7.1 | 6.4 | <0.05 |

Comparison of the data presented in Tables 2 and 4 clearly shows that the simple acidification step followed by an industrially feasible decantation, filtration or low speed centrifugation step results in a 5-fold increase in the concentration of the specific ACE inhibiting peptides if calculated per gram of protein present in the supernatant. This 5-fold increase in concentration was obtained without any optimisation of the acid precipitation procedure used. To get an impression of the amino acid composition of this acid soluble fraction containing these enhanced levels of ACE inhibiting peptides, the peptides present were acid-hydrolysed and then subjected to an amino acid analysis according to Waters (see Materials & methods section). According the results obtained the acid soluble protein fraction according to the invention has a proline content of almost 24% on a molar basis and 21% on a weight basis of the peptides present in this fraction! This observation is quite surprising as proline is known as one of the most hydrophobic amino acids so finding enhanced proline levels in the acid soluble fraction is unexpected. In fact peptide fractions obtained in a this acidification step containing that high an amount of proline are new. For example gelatin, known as the most proline rich protein, contains apart from 14.4% (w/w) of hydroxyproline, only 16.5% (w/w) of proline.

Example 7

The Aminopeptidolytic Activity of Different Commercial Enzyme Preparations

In beta-casein IPP is contained in the sequence -$P_{71}$-$Q_{72}$-$N_{73}$-$I_{74}$-$P_{75}$-$P_{76}$-, VPP is contained in the sequence -$P_{81}$-$V_{82}$-$V_{83}$-$V_{84}$-$P_{85}$-$P_{86}$- and LPP is contained in the sequence -$P_{150}$-$L_{151}$-$P_{152}$-$P_{153}$-. Of the other protein constituents of casein only kappa-casein incorporates an IPP containing sequence. From the specificity of the proline specific endoprotease it can be inferred that upon incubating beta-casein with the *A. niger* derived enzyme the peptides $Q_{72}$-$N_{73}$-$I_{74}$-$P_{75}$-$P_{76}$-, $V_{82}$-$V_{83}$-$V_{84}$-$P_{85}$-$P_{86}$- and $L_{151}$-$P_{152}$-$P_{153}$- will be formed. In contrast with LPP, the two pentapeptides formed exhibit low ACE inhibiting activities only. For example EP 0 583 074 reports an $IC_{50}$ value for VVVPP of 873 micromole/l whereas the truncated VPP molecule has an $IC_{50}$ value of 9 micromole/l. So it is obvious that for generating the full ACE inhibiting potential of a casein hydrolysate, the pentapeptides VVVPP and QNIPP that are formed upon incubation with the proline specific endoprotease have to be transformed into the tripeptides VPP and IPP respectively. As aminopeptidases can sequentially remove amino acids from the N-terminal side of peptides, an aminopeptidolytic enzyme activity is required that can efficiently liberate the two valine ("V") residues preceding the VPP sequence and the glutamine ("Q") and asparagine ("N") residues that precede the IPP sequence. Because the X-P and P-P peptide bonds present in XPP tripeptides are known to resist enzymatic cleavage, it is likely that such an aminopeptidolytic activity will transform the two pentapeptides into the desired VPP and IPP tripeptides.

Three commercial enzyme preparations were tested for their aminopeptidolytic activities i.e.: Flavourzyme 1000L Batch HPN00218 (Novozymes), Sumizyme FP (Shin Nihon) and Corolase LAP Ch.: 4123 (AB Enzymes). Both Flavourzyme and Sumizyme FP are known to be complex enzyme preparations that contain several aminopeptidolytic enzyme activities besides non-specified endoproteolytic and carboxypeptidolytic activities. Corolase LAP represents a relatively pure, cloned and overexpressed leucine aminopeptidase activity from *Aspergillus*.

Figure 4:
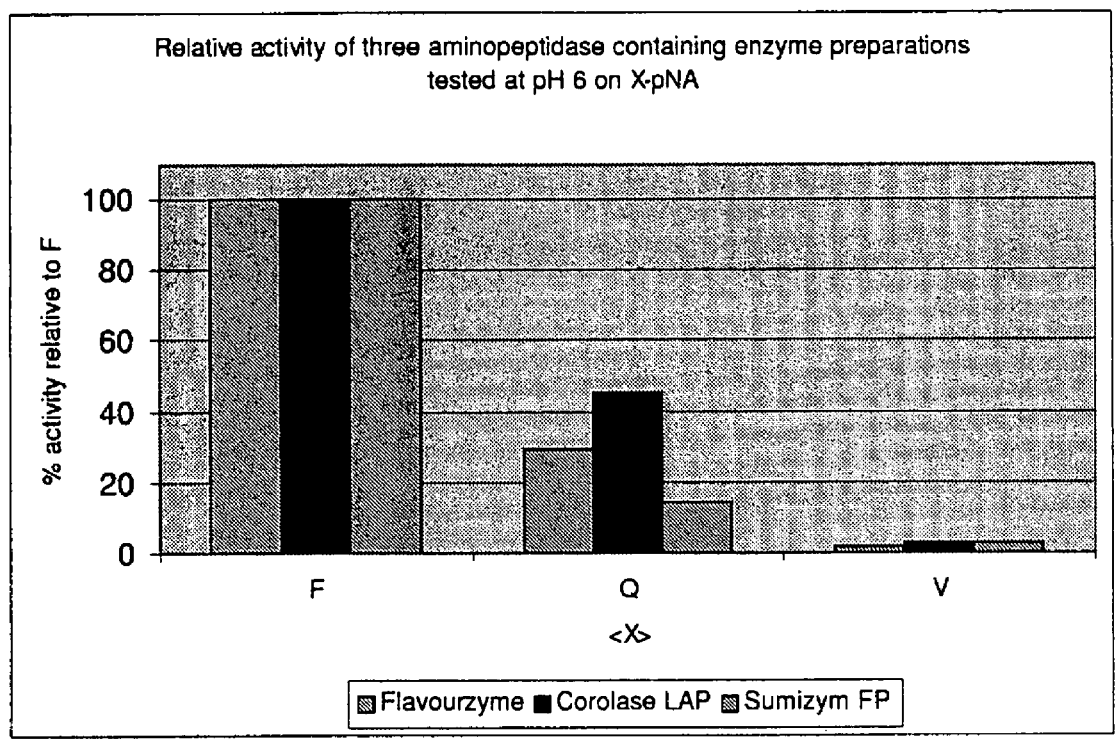
FIG. 4: Relative activity of three commercially available aminopeptidase containing enzyme preparations tested at pH 6.0 on the synthetic substrates F-pNA, Q-pNA and V-pNA.

The aminopeptidolytic activities present in these three commercial preparations were tested using the chromogenic substrates F-pNA (reference), Q-pNA and V-pNA. To that end a stock solution of 150 mM X-pNA in DMSO was diluted 100× in Bis-Tris buffer pH 6. A microtiter plate was filled with 200 µl buffered substrate solution per well and pre-incubated at 40° C. in a Tecan Genios MTP reader, controlled by Magellan 4 software. The reaction was started by adding 50 µl of the appropriate enzyme solution (the Sumizyme FP powder was dissolved in Bis-Tris buffer pH 6 in a concentration of 100 mg/ml prior to use). Liberation of the yellow pNA is followed at 405 nm for 10 minutes. The software calculates the OD/min. The activity of each enzyme preparation towards the various substrates was standardised relative to their activity towards F-pNA. The data obtained are shown in FIG. 4. Evidently all three enzyme preparations display the highest activity towards F-pNA but Q-pNA and V-pNA form substrates for these enzymes as well. These results indicate that if combined with a proline specific protease each one of the commercial preparations should be capable of forming the desired ACE inhibiting tripeptides IPP, VPP as well as LPP because the activity of the aminopeptidase will convert the peptides QNIPP and VVVPP formed by the proline specific protease into IPP and VPP respectively. This hypothesis was tested in an experiment described in Example 8.

Example 8

Incubating Caseinate with the Proline Specific Endoprotease from *A. niger* Together with Different Aminopeptidolytic Enzyme Preparations Generates High Yields of IPP, LPP and VPP The enzymatic route towards IPP and VPP as described in EP 1 231 279 requires a two-step process. During the first step in which the casein is incubated with a suitable proteinase, larger intermediate peptides are formed some of which encompass either IPP or VPP. According to one of the Examples described in EP 1 231 279 incubation with this proteinase is carried out at 37 degrees C. for a 12 hours period. Then the proteinase used is inactivated by heating this first hydrolysate to 100 degrees C. for 3 minutes and, after cooling down again, another enzyme preparation (in fact a preparation with exoproteolytic activity) is added. This incubation with an exoproteolytic activity forms the second step. After another 12 hours incubation at 37 degrees C. with this second enzyme preparation the presence of the tripeptides Val-Pro-Pro and Ile-Pro-Pro can be demonstrated. To obtain higher yields of these ACE inhibiting peptides, EP 1 231 279 further suggests to purify and concentrate the intermediate peptide prior to exposure to the exoproteolytic activity. EP 1 231 279 also suggests that after obtaining the intermediate peptide and before the intermediate peptide is contacted with the peptidase in the procedure various operations may optionally be performed such as the removal of the unreacted protein by e.g. centrifugation at 5000 to 20000 rpm for 3 to 10 minutes. So the desired tripeptides are obtained in an industrially rather unwieldy two-step enzymatic process. As each of the enzyme incubations may take as long as 12 hours at pH 4.5 to 7.0 and at the temperature of 25 to 50 degrees C., it is evident that this procedure is also unacceptable from a microbiological point of view.

In the present Example we investigate the effect of combining the proline specific protease from *A. niger* with an aminopeptidolytic activity in a single incubation step on the formation of various ACE inhibiting peptides. To that end a caseinate solution was prepared by dissolving 50 gram sodium caseinate into 506 grams of water of 70 degrees C. to yield a solution containing 81 grams of protein/l. This solution was cooled down to 50 degrees C. after which the pH was lowered to 6.0 (measured at 20° C.) using phosphoric acid after which various enzyme combinations were added. To all samples (10 ml each) the proline specific protease was added to reach a concentration of 4 units per gram of protein (see the Materials & Methods section for unit definition). Sample A1 contained only this proline specific protease. Sample B1 contained the proline specific protease plus 38 microliter of a solution containing 1140 mg of the concentrated Flavourzyme liquid diluted in 5 grams of water. In sample B2 the proline specific protease was combined with 8 microliter of this Flavourzyme solution. In sample C1 the proline specific protease was combined with 100 microliter of the Corrolase LAP liquid. In sample C2 the proline specific protease was combined with 10 microliter of a 10 times diluted sample of the Corrolase LAP liquid. In all 5 samples incubation was allowed to proceed for 6 hours at 50 degrees C. The enzyme reactions were terminated by heating the mixture for 5 minutes to 90 degrees C. Clear supernatants obtained after centrifugation for 10 minutes in an Eppendorf centrifuge were collected and kept frozen until LC/MS/MS analysis. The data as obtained after LC/MS/MS analysis are shown in Table 5.

As demonstrated before the incubation condition of sample A1 (with just the proline specific protease present) efficiently generates LPP as well as VVVPP, but no significant quantities of VPP. The absence of peptide VVVPPF illustrates that the proline specific protease efficiently cleaves carboxyterminal of proline residues under the conditions as applied. In sample A1 the yield of IPP is roughly a third of the yield of VVVPP. However, combining the proline specific protease with either Flavourzyme (samples B1 and B2) or with Corrolase LAP (sample C1) has a clear stimulatory effect on IPP yields. In sample C2 (with a low concentration of Corrolase LAP) the yield of IPP was not increased, presumably because the concentration of the aminopeptidase activity was inadequate to convert all QNIPP formed by the proline specific protease. As 1 gram of casein can theoretically yield 6.9 mg (21.1 micromole) of IPP (from the beta-casein plus the kappa-casein), the IPP levels present in samples B1 and C1 represent 70% and 55% respectively of the maximal obtainable yields. In line with our expectations the increasing aminopeptidolytic activity results in a lowering of the VVVPP concentration and an increase in the VPP concentration. The fact that small quantities of the intermediate peptide VVPP are detectable in samples B2 and C2 indicates that in these samples the aminopeptidolytic activity is inadequate to fully convert the VVVPP formed by the proline specific protease into VPP. As 1 gram of casein can theoretically yield 4.58 mg (14.7 micromole) of VPP, in samples B1, B2 and C1 the maximal VPP yield is reached.

In conclusion the present experiment clearly demonstrates that the combination of a proline specific protease with an suitable aminopeptidolytic activity can efficiently generate high concentrations of the ACE inhibiting peptides in a single enzyme incubation step and at temperatures of 50 degrees C. or higher.

TABLE 5

| | Peptide concentrations in supernatants calculated in mg/g protein added | | | | | |
|---|---|---|---|---|---|---|
| sample | IPP | LPP | VPP | VVPP | VVVPP | VVVPPF |
| A1 | 1.0 | 3.4 | 0.1 | <0.05 | 4.6 | <0.05 |
| B1 | 4.8 | 1.3 | 4.6 | <0.05 | 0.05 | <0.05 |

TABLE 5-continued

| sample | Peptide concentrations in supernatants calculated in mg/g protein added | | | | | |
|---|---|---|---|---|---|---|
| | IPP | LPP | VPP | VVPP | VVVPP | VVVPPF |
| B2 | 3.0 | 3.0 | 5.0 | 0.7 | 0.6 | <0.05 |
| C1 | 3.8 | 3.8 | 4.8 | nd | <0.05 | <0.05 |
| C2 | 1.4 | 3.5 | 1.8 | 0.9 | 1.3 | <0.05 | nd = not detectable

Example 9

The Quantitation of Desirable and Contaminating Enzyme Activities in the Production of ACE Inhibiting Peptides According to the present invention ACE inhibitory peptides can be obtained in a simple one-step process by selectively recovering IPP, VPP and LPP from a casein substrate by incubation with a proline specific endoprotease plus an aminopeptidase. Subsequent enrichment of these solubilised ACE inhibitory peptides is accomplished by precipitating the remaining larger molecular weight protein by acidification or by adding a water miscible organic solvent. During this selective recovery process, the presence of any contaminating endoproteases or carboxypeptidases negatively influences the quality of the final tripeptide mixture. For example, the presence of non-proline or non-alanine specific endoproteases leads to the solubilisation of additional, non-bioactive peptides hereby diluting the relative concentrations of IPP, LPP and VPP in the final concentrate. Furthermore the presence of contaminating exoproteases such as for example carboxypeptidases, results in ACE inhibitory peptide preparations having increased levels of free amino acids. These extra free amino acids also dilute the relative concentrations of IPP, LPP and VPP and, moreover, impart brothy off tastes as the result of increased Maillard reactions. To minimise all these undesirable side reactions, the combination of an essentially pure proline specific protease with an essentially pure aminopeptidase is preferred. Essentially pure meaning that the activity of contaminating endoproteases as well as contaminating carboxypeptidases under the incubation conditions used are minimal or preferably absent. The following testing procedure was devised to quantitate such contaminating endo- and carboxypeptidases activities.

The basis for the testing procedure is formed by a collection of various selective chromogenic peptides. Because only proline specific oligo- and endoproteases can release pNA from peptide Z-AAAP-pNA, this particular peptide was used to quantitate the desired proline specific endoproteolytic activity. Because many endoproteases can release pNA from peptides Z-AAAF-pNA and Z-AAAR-pNA, these two peptides were used to quantitate contaminating, non-proline specific endoproteolytic activity. Because the conversion of peptides QNIPP and VVVPP into IPP and VPP respectively require aminopeptidases that can efficiently remove Gln and Val residues, peptides Q-PNA and V-pNA were used to quantitate desired aminopeptidase activities. Because many carboxypeptidases can release Phe and Arg residues from peptides, peptides containing these residues were selected to quantitate contaminating carboxypeptidase activities. However, no suitable chromogenic groups are available for measuring carboxypeptidase activities so that an alternative method using the synthetic peptides Z-AF and Z-AR had to be developed. This alternative method is provided underneath.

In all the synthetic peptides used "Z" represents benzyloxycarbonyl and "pNA" the chromophore para-nitroanilide. All chromogenic peptides were obtained from Pepscan (Lelystad, The Netherlands). Peptides Z-AF and Z-AR were purchased from Bachem (Switzerland). All incubations were carried out at 40° C. Diluted enzyme preparations were recalculated to the concentration of the commercial product.

Measuring Amino Peptidase Activities

Stock solutions of 150 mmol/l of V-pNA and Q-pNA in 100% DMSO were diluted 80 times in 0.1 M BisTris buffer pH 6 to make a 3.75 mmol/l V-pNA+Q-pNA-substrate solution containing V-pNA and Q-pNA in a 1:1 ratio. A 200 µl aliquot of this aminopeptidase substrate solution was pipetted into separate wells of a microtiter plate (MTP) The MTP is pre-incubated at 40° C. in a Tecan Genios MTP (Salzburg, Vienna) running under Magellan4 software. The reaction was started by adding 50 µl of the appropriate enzyme solution so that the incubations took place at a substrate concentration of 3 mM. Typically a 1:50 dilution of the liquid enzyme samples Flavourzyme, Corolase LAP and proline-specific endo-protease was used. Of the dry Sumizyme FP product a 1% solution was used.

The yellow color as measured at 405 nm by the Tecan Genios MTP developing as the result of cleavage of the amino acid-pNA bond was followed for at least 20 kinetic cycles (about 10 minutes). The software generated the data obtained as $OD_{405}$/min.

Measuring Proline Specific Endoprotease Activity

This measurement was carried out essentially the same as the aminopeptidase assay but in this case Z-AAAP-pNA was used as the only substrate in a final concentration of 3 mmol/l. This substrate was solubilized by heating a suspension in pH 6 buffer to 50-55° C. resulting in a clear solution at room temperature. Measurements were carried out at 40° C.

Typically a 1:50 dilution of the liquid enzyme samples Flavourzyme and Corolase LAP were used. Sumizyme FP was used in a 1% solution. The proline specific endo-protease was typically used in a 1:5000 dilution.

The software generated the data as $OD_{405}$/min.

Measuring Contaminating Non-Proline Specific Endoprotease Activities.

Also this measurement was carried out essentially the same as described for the aminopeptidase assay but in this test Z-AAAF-pNA and Z-AAAR-pNA in a 1:1 ratio and in a final concentration of 3 mmol/l were used as the substrate. The substrate Z-AAAF-pNA turned out to be poorly soluble under the pH 6.0 test conditions used but a test incubation with subtilisin resulted in a rapid solubilisation of the substrate concomitantly with the pNA release. Measurements were carried out at 40° C. However, to compensate for this poor solubility the MTP reader was programmed to shake in between the kinetic cycles.

Again the software generated the data as $OD_{405}$/min.

Measuring Contaminating Carboxypeptidase Activities

Because no sensitive chromogenic peptides are available to measure carboxypeptidase activities, a method was used based on a Boehringer protocol for quantitating Carboxypeptidase C.

Two 150 mmol/l stock solutions in ethanol of Z-A-F and Z-A-R were diluted 80 times in 0.1 mol/l BisTris buffer pH 6 to make a 3.75 mmol/l Z-A-F+Z-A-R substrate solution containing Z-A-F and Z-A-R in a 1:1 ratio. Then 200 µl of the substrate solution was pipetted into an eppendorf vial and pre-incubated at 40° C. The reaction was started by adding 50 µl of an appropriate enzyme dilution. Typically a 1:50 dilution is used of Flavourzyme and Corolase LAP and the proline specific endoprotease. A 1% solution was used for Sumizym FP. After 5 minutes the reaction was stopped by adding 250 µl of ninhydrine reagent. Ninhydrine reagent was made of 400 mg ninhydrine (Merck) and 60 mg hydrindantin dissolved 15 ml DMSO, to which 5 ml of 4.0 mol/l lithium acetate buffer pH 5.2 was added. The 4.0 mol/l lithium acetate buffer was made by dissolving LiOH (Sigma) after which the pH of the solution was adjusted to pH 5.2 using glacial acetic acid (Merck).

After stopping the reaction, each sample was heated for 15 minutes at 95° C. to facilitate the color formation and subsequently diluted 10 times with pure ethanol. The color formed was measured at 578 nm in an Uvikon spectrophotometer. Blanks were made in the same manner as the activity samples, but ninhydrin reagent and enzyme addition were reversed. To quantitate the amount of free amino acids generated by the carboxypeptidase activity, the amino acid L-phenylalanine was used to create a calibration curve. Solutions in buffer pH 6 containing 0.1875, 0.375, 0.75, 1.5 and 3.0 mmol/l of L-phenylalanine (Sigma) were treated in the same manner as the samples, i.e. 250 µl in a vial. From the OD578 values obtained, a curve was constructed in Excel. The concentrations of the free amino acids present in the samples containing the Z-A-F and Z-A-R substrates were calculated using this curve. From the values obtained the carboxy-peptidase activity was calculated in micromoles per minute per the amount of enzyme tested.

Calculation of Activity Ratios

To establish the suitability of various enzyme preparations for the process according to the invention, quotients of the relevant enzyme activities were calculated. In the MTP reader based assays, enzyme activities are characterised by pNA release over time i.e. as $_?OD_{405}$/Min. Quotients of enzyme activities obtained by the MTP reader were calculated by simply dividing the $_?OD$/min values obtained for identical quantities of enzyme.

However in case of the carboxy-peptidase assay, an OD is generated that cannot be compared directly to the $_?OD$/min generated by the MTP-pNA based assays. Here the OD measured was first converted to µmol amino acid released per min (µmol/min). Then the $_?OD$/min of pNA released was converted into µmol/min. To that end a calibration curve was generated in the MTP reader in which dilutions of pure pNA (Sigma) 0.25, 0.125, 0.0625, 0.0312 and 0.015 mmol/l and 250l per well were measured. From the data obtained a calibration curve was constructed in Excel. From this calibration curve the ?OD/min was converted into µmol/min so that the pNA based measurements could be compared with the ninhydrin based measurements.

On the basis of the data generated in the above-mentioned tests, the various enzyme preparations used were characterised in terms of desirable proline specific and aminopeptidase activities and contaminating endoprotease and carboxypeptidase activities. Furthermore enzyme combination C1 used in Example 8 and consisting of a mixture of 4 units proline specific endoprotease and 130 microliter of Corolase LAP per gram of casein resulting in an optimal release of ACE inhibitory peptides after an incubation period of 6 hours at 50 degrees C., was characterized in this way. The data on the proline specific oligo- or endoproteolytic activities present in each enzyme preparation as provided are shown in Table 6 in the column "Prol Spec Activity". The data on the desired aminopeptidase activities (AP/Prol Spec Act) and the contaminating carboxypeptidase (CPD/Prol Spec Act) and endoproteolytic activities (Endo/Prol Spec Act) are shown relative to the proline specific activities present. The desired aminopeptidase activity relative to the contaminating carboxypeptidase activity as present in each preparation is shown as (AP/CPD).

Evident is that none of the commercial enzyme preparations tested contains any significant proline specific oligo- or endoproteolytic activity. Furthermore all commercial enzyme preparations tested contain contaminating carboxypeptidase and endoproteolytic activities. Enzyme combination C1 that generates high yields of ACE inhibiting IPP, VPP and LPP peptides stands out because of its very low levels of contaminating carboxypeptidase and endoproteolytic activities.

TABLE 6

|  | Prol Spec Activity* | CPD/Prol spec act | AP/Prol spec act | Endo/ Prol spec act | AP/ CPD |
|---|---|---|---|---|---|
| Sumizyme | 0.004 | 21.7 | 1.2 | 1.7 | 0.06 |
| Flavourzyme | 0.0007 | 253.5 | 25.6 | 35.5 | 0.10 |
| Corolase LAP | 0.0 |  |  |  | 0.74 |
| Prol spec A. niger | 100 | 0.005 | 0.00001 | 0.000004 | 0.00 |
| C1 | 75 | 0.001 | 0.00031 | 0.000391 | 0.25 |

*Sumizyme was measured in a 1% solution, Flavourzyme and Corolase as a 1:50 dilution. Prol specific activity as obtained from A. niger was measured as 1:5000 dilution and C1 as a 1:3773 dilution. Data were then calculated to the activity present in the product as provided.

The invention claimed is:

1. A process to produce IPP and VPP from a protein source that comprises the -I-P-P- and -V-P-P- sequence in its protein sequence and whereby at least 40% of -I-P-P-sequence present in the protein source is converted into the peptide IPP and at least 40% of the -V-P-P- sequence present in the protein source is converted into the peptide VPP, which comprises the use of a proteolytic enzyme which cleaves at the carboxy terminus of proline and an amino peptidase, wherein the proteolytic enzyme which cleaves at the carboxy terminus of proline and the amino peptidase are incubated together in a single step.

2. A process according to claim 1 whereby the protein source comprises the -L-P-P- sequence in its protein sequence and at least 40% of the -L-P-P- sequence present in the protein source is converted into the peptide LPP.

3. A process according to claim 1 wherein the incubation time is less than 24 hrs.

4. A process according to claim 1 wherein the incubation temperature is higher than 30° C.

5. A process according to claim 1 wherein said protein source is a milk protein.

6. A process according to claim 1 wherein -I-P-P- or -V-P-P- sequence present in the protein sequence is converted for at least 50% into the peptide IPP or VPP.

7. A protest according to claim 1 which further comprises separation of soluble peptides, including IPP and VPP, from the hydrolysed protein by precipitation under selected pH conditions, which comprises altering the pH to the pH whereby part of the hydrolysed protein precipitates and separating the precipitated material from the dissolved peptides.

8. A process according to claim 1 which further comprises separation of soluble peptides from hydrolysed protein, which comprises adding a water miscible solvent to the hydrolysed protein whereby part of the hydrolysed protein precipitates and separating the precipitated material from the dissolved peptides.

9. The process according to claim 1 wherein the proteolytic enzyme which cleaves at the carboxy terminus of protein is a proline specific endoprotease or a praline specific oligopeptidase.

10. The process according to claim 1 wherein the proteolytic enzyme which cleaves at the carboxy terminus of proline is a proline specific endoprotease.

11. The process according to claim 3 wherein the incubation time is less than 10 hours.

12. The process according to claim 11 wherein the incubation time is less than 4 hours.

13. The process according to claim 4 wherein the incubation temperature is higher than 40° C.

14. The process according to claim 13 wherein the incubation temperature is higher than 50° C.

15. The process according to claim 5 wherein the milk protein is casein or a caseinate.

16. The process according to claim 15 wherein the milk protein is potassium, calcium, magnesium or ammonia caseinate.

17. The process according to claim 6 wherein -I-P-P- or -V-P-P- sequence present in the protein sequence is converted for at least 60% into the peptide IPP or VPP.

18. The process according to claim 7 wherein the pH is altered to a pH between 3.5 and 6.

19. The process according to claim 18 wherein the pH is altered to a pH between 4 and 5.

* * * * *